United States Patent
Frutos et al.

(10) Patent No.: US 7,604,984 B2
(45) Date of Patent: Oct. 20, 2009

(54) SPATIALLY SCANNED OPTICAL READER SYSTEM AND METHOD FOR USING SAME

(75) Inventors: Anthony G. Frutos, Painted Post, NY (US); Jacques Gollier, Painted Post, NY (US); Jinlin Peng, Painted Post, NY (US); Garrett A. Piech, Horseheads, NY (US); Michael B. Webb, Lindley, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 11/027,547

(22) Filed: Dec. 29, 2004

(65) Prior Publication Data

US 2006/0141611 A1 Jun. 29, 2006

(51) Int. Cl.
*C12M 1/34* (2006.01)
*G01N 21/00* (2006.01)
*G01N 21/01* (2006.01)
*G01J 3/00* (2006.01)
*G01J 3/28* (2006.01)
*G02B 6/00* (2006.01)
*G02B 6/34* (2006.01)
*G02B 26/08* (2006.01)
*G02F 1/07* (2006.01)

(52) U.S. Cl. ............... 435/288.7; 422/82.05; 422/82.09; 422/82.11; 385/12; 385/37; 356/244; 356/73.1; 356/300; 356/328; 359/263; 359/196; 436/164

(58) Field of Classification Search ............... 422/82.05, 422/82.09, 82.11; 385/12, 37; 356/244, 356/73.1, 300, 328; 359/263, 196; 435/288.7; 436/164

See application file for complete search history.

(56) References Cited

U.S. PATENT DOCUMENTS 4,710,031 A 12/1987 Kelly et al. .................. 356/440

(Continued)

FOREIGN PATENT DOCUMENTS

EP 0 202 021 11/1986

OTHER PUBLICATIONS

J. Dübendorfer et al., "Sensing and Reference Pads for Integrated Optical Immunosensors", Journal of Biomedical Optics, vol. 2, No. 4, Oct. 1997, pp. 391-400.

(Continued)

*Primary Examiner*—Bao-Thuy L Nguyen
*Assistant Examiner*—Jacqueline Diramio
(74) *Attorney, Agent, or Firm*—Timothy M Schaeberle; Thomas R Beall; William J Tucker

(57) ABSTRACT

An optical reader system is described herein that uses a scanned optical beam to interrogate a biosensor to determine if a biomolecular binding event occurred on a surface of the biosensor. In one embodiment, the optical reader system includes a light source, a detector and a processor (e.g., computer, DSP). The light source outputs an optical beam which is scanned across a moving biosensor and while this is happening the detector collects the optical beam which is reflected from the biosensor. The computer processes the collected optical beam and records the resulting raw spectral or angle data which is a function of a position (and possibly time) on the biosensor. The processor can then analyze the raw data to create a spatial map of resonant wavelength (peak position) or resonant angle which indicates whether or not a biomolecular binding event occurred on the biosensor. Several other uses of the raw data are also described herein.

2 Claims, 21 Drawing Sheets

U.S. PATENT DOCUMENTS

| | | | | |
|---|---|---|---|---|
| 4,815,843 | A | 3/1989 | Tiefenthaler et al. | 356/128 |
| 4,992,385 | A | 2/1991 | Godfrey | 436/525 |
| 5,047,651 | A * | 9/1991 | Wessner et al. | 250/548 |
| 5,310,686 | A | 5/1994 | Sawyers et al. | 436/518 |
| 5,340,715 | A | 8/1994 | Slovacek et al. | 435/6 |
| 5,592,289 | A | 1/1997 | Norris | 356/244 |
| 5,631,170 | A | 5/1997 | Attridge | 436/518 |
| 5,738,825 | A | 4/1998 | Rudiger et al. | 422/82.11 |
| 5,822,073 | A | 10/1998 | Yee et al. | 356/445 |
| 6,258,326 | B1 | 7/2001 | Modlin | 422/102 |
| 6,312,961 | B1 | 11/2001 | Voirin et al. | 436/518 |
| 6,346,376 | B1 | 2/2002 | Sigrist et al. | 435/5 |
| 6,455,004 | B1 | 9/2002 | Tiefenthaler | |
| 6,709,869 | B2 * | 3/2004 | Mian et al. | 436/45 |
| 6,738,141 | B1 | 5/2004 | Thirstrup | 356/445 |
| 6,787,110 | B2 | 9/2004 | Tiefenthaler | |
| 6,829,073 | B1 * | 12/2004 | Krol et al. | 359/263 |
| 6,884,628 | B2 | 4/2005 | Hubbell et al. | 436/518 |
| 7,057,720 | B2 | 6/2006 | Caracci et al. | 356/300 |
| 2002/0009391 | A1 | 1/2002 | Marquiss et al. | 422/63 |
| 2002/0090320 | A1 | 7/2002 | Burow et al. | 422/64 |
| 2002/0127565 | A1 | 9/2002 | Cunningham et al. | 435/6 |
| 2002/0132261 | A1 * | 9/2002 | Dorsel et al. | 435/6 |
| 2002/0168295 | A1 | 11/2002 | Cunningham et al. | 422/82.05 |
| 2003/0007896 | A1 | 1/2003 | Tiefenthaler | 422/91 |
| 2003/0017580 | A1 | 1/2003 | Cunningham et al. | 435/287.2 |
| 2003/0017581 | A1 | 1/2003 | Li et al. | 435/287.2 |
| 2003/0026891 | A1 | 2/2003 | Qiu et al. | 427/58 |
| 2003/0027327 | A1 | 2/2003 | Cunningham et al. | 435/287.2 |
| 2003/0027328 | A1 | 2/2003 | Cunningham et al. | 435/287.2 |
| 2003/0032039 | A1 | 2/2003 | Cunningham et al. | 435/6 |
| 2003/0059855 | A1 | 3/2003 | Cunningham et al. | 435/7.9 |
| 2003/0067612 | A1 | 4/2003 | Ivarsson | 356/600 |
| 2003/0068657 | A1 | 4/2003 | Lin et al. | 435/7.9 |
| 2003/0077660 | A1 | 4/2003 | Pien et al. | 435/7.1 |
| 2003/0092075 | A1 | 5/2003 | Pepper | 435/7.9 |
| 2003/0113766 | A1 | 6/2003 | Pepper et al. | 435/6 |
| 2003/0133640 | A1 | 7/2003 | Tiefenthaler | 385/12 |
| 2003/0169417 | A1 | 9/2003 | Atkinson et al. | 356/135 |
| 2003/0219809 | A1 | 11/2003 | Chen et al. | 435/6 |
| 2004/0091397 | A1 * | 5/2004 | Picard | 422/99 |
| 2004/0132172 | A1 | 7/2004 | Cunningham et al. | 435/287.2 |
| 2004/0132214 | A1 | 7/2004 | Lin et al. | 436/518 |
| 2004/0132606 | A1 | 7/2004 | Wolff et al. | 601/66 |
| 2004/0151626 | A1 | 8/2004 | Cunningham et al. | 422/58 |
| 2004/0166496 | A1 | 8/2004 | Leproust et al. | 435/6 |
| 2004/0223881 | A1 | 11/2004 | Cunningham et al. | 422/82.05 |
| 2004/0247486 | A1 | 12/2004 | Tiefenthaler | |
| 2005/0014135 | A1 | 1/2005 | Hill et al. | 435/5 |
| 2005/0070027 | A1 | 3/2005 | Gollier et al. | 436/518 |
| 2005/0088648 | A1 | 4/2005 | Grace et al. | 356/318 |
| 2005/0099622 | A1 | 5/2005 | Caracci et al. | 356/300 |
| 2005/0153290 | A1 * | 7/2005 | Van Beuningen | 435/6 |
| 2005/0236554 | A1 | 10/2005 | Fontaine et al. | 250/208.1 |
| 2006/0106557 | A1 | 5/2006 | Fontaine et al. | 702/87 |
| 2006/0141527 | A1 | 6/2006 | Caracci et al. | 435/7.1 |

OTHER PUBLICATIONS

K. Tiefenthaler et al., "Integrated Optical Switches and Gas Sensors", Optics Letters, vol. 10, No. 4, Apr. 1984, pp. 137-139.

M. Wiki et al., "Wavelength-Interrogated Optical Sensor for Biochemical Applications", Optics Letters, vol. 25, No. 7, Apr. 1, 2000, pp. 463-465.

K. Cottier et al., "Label-Free Highly Sensitive Detection of (Small) Molecules by Wavelength Interrogation of Integrated Optical Chips", Sensors and Actuators B, vol. 91, 2003, pp. 241-251.

K. Tiefenthaler et al., "Sensitivity of Grating Couplers as Integrated-Optical Chemical Sensors", J. Opt. Soc. Am. B., vol. 6, No. 2, Feb. 1989, pp. 209-220.

W. Lukosz, "Integrated Optical Chemical and Direct Biochemical Sensors", Sensors and Actuators B, vol. 29, 1995, pp. 37-50.

M. Wiki et al., "Novel Integrated Optical Sensor Based on a Grating Coupler Triplet", Biosensors & Bioelectronics, vol. 13, 1998, pp. 1181-1185.

M.J. O'Brien II et al., "SPR Biosensors: Simultaneously Removing Thermal and Bulk-Composition Effects", Biosensors & Bioelectronics, vol. 14, 1999, pp. 145-154.

L.G. Mendoza et al., High-Throughput Microarray-Based Enzyme-Linked Immunosorbent Assay (ELISA), BioTechniques, vol. 27, No. 4, 1999, pp. 778-788.

J.X. Huang et al., "High-Throughput Genomic and Proteomic Analysis Using Microarray Technology", Clinical Chemistry, vol. 47, No. 10, pp. 1912-1916.

T. Wilkop et al., "Analysis of μ-Contact Printed Protein Patterns by SPR Imaging with a LED Light Source", Langmuir, 2004, vol. 20, pp. 11141-11148.

T.E. Plowman et al., "Multiple-Analyte Fluoroimmunoassay Using an Integrated Optical Waveguide Sensor", Analytical Chemistry 1999, vol. 71, No. 19, Oct. 1, 1999, pp. 4344-4352.

D. Nedelkov et al., "Surface plasmon resonance mass spectrometry: recent progress and outlooks". TRENDS in Biotechnology, vol. 21, No. 7, Jul. 2003, pp. 301-305.

M. Bilban et al., "Normalizing DNA Microarray Data", Curr. Issues Mol. Bol., 2002, vol. 4, pp. 57-64.

Q. Xu et al., "Protein and Chemical Microarrays—Powerful Tools for Proteomics", Journal of Biomedicine and Biotechnology, 2003, vol. 5, pp. 257-266.

S. Venkatasubbarao, "Microarrays—status and prospects", TRENDS in Biotechnology, vol. 22, No. 12, Dec. 2004, pp. 630-637.

M. Schaferling et al., "Protein Microarray Surface Chemistry and Coupling Schemes", Protein Microarray Technology, Jan. 15, 2004, ISBN: 3-527-30597-1, URL:http://www3.interscience.wiley.com/cgi-bin/booktext/107061764/BOOKPDFSTART>, pp. 11-38.

* cited by examiner

\* Units are pm in vertical
and mRd in horizontal

SPATIALLY SCANNED OPTICAL READER SYSTEM AND METHOD FOR USING SAME

CROSS REFERENCE TO RELATED APPLICATION

This application is related to U.S. patent application Ser. No. 11/027,509 filed concurrently herewith and entitled "Method for Creating a Reference Region and a Sample Region on a Biosensor and the Resulting Biosensor" the contents of which are hereby incorporated by reference herein.

BACKGROUND OF THE INVENTION

1. Field of the Invention

The present invention relates to an optical reader system that uses a scanned optical beam to interrogate one or more biosensors. In one embodiment, the biosensors are incorporated within the wells of a microplate.

2. Description of Related Art

Manufacturers of optical reader systems are always trying to design a new and improved optical reader system that can be used to interrogate a resonant waveguide grating biosensor to determine if a biomolecular binding event (e.g., binding of a drug to a protein) occurred on a surface of the biosensor. One such new and improved optical reader system is the subject of the present invention.

BRIEF DESCRIPTION OF THE INVENTION

The present invention includes an optical reader system that uses a scanned optical beam to interrogate a resonant waveguide grating biosensor to determine if a biomolecular binding event occurred on a surface of the biosensor. In one embodiment, the optical reader system includes a light source, a detector and a processor (e.g., computer, DSP). The light source outputs an optical beam which is scanned across a moving biosensor and while this is happening the detector collects the optical beam which is reflected from the biosensor. The computer processes the collected optical beam and records the resulting raw spectral or angle data which is a function of a position (and possibly time) on the biosensor. The processor can then analyze the raw data to create a spatial map of resonant wavelength (peak position) or resonant angle which indicates whether or not a biomolecular binding event occurred on the biosensor. Several other uses of the raw data are also described herein.

BRIEF DESCRIPTION OF THE DRAWINGS

A more complete understanding of the present invention may be had by reference to the following detailed description when taken in conjunction with the accompanying drawings wherein.

DETAILED DESCRIPTION OF THE DRAWINGS

Figure 1A:
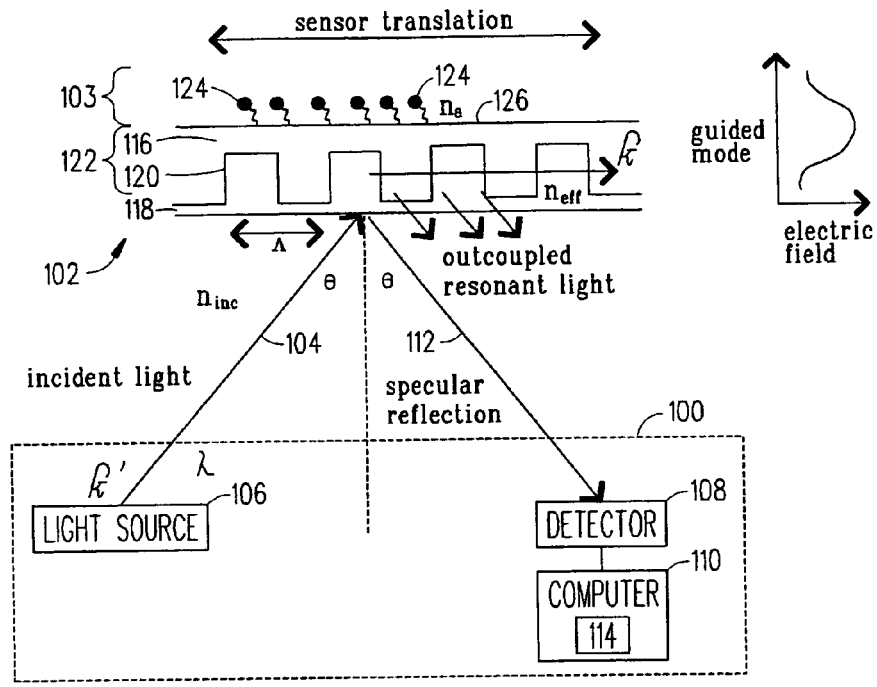
FIGS. 1A and 1B respectively illustrate a block diagram of the optical reader system and a flowchart of the method for using the optical reader system in accordance with one embodiment of the present invention.
Figure 1B:
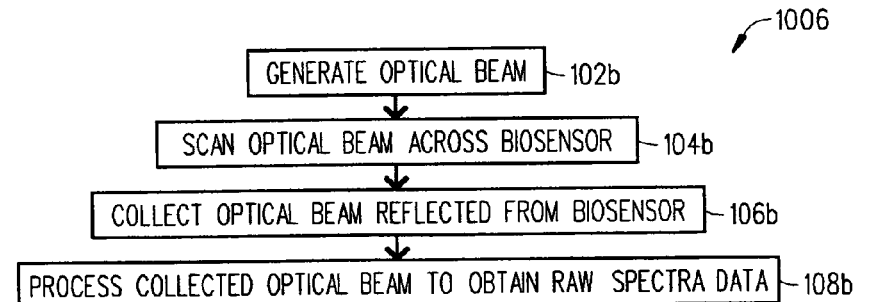
Figure 2:
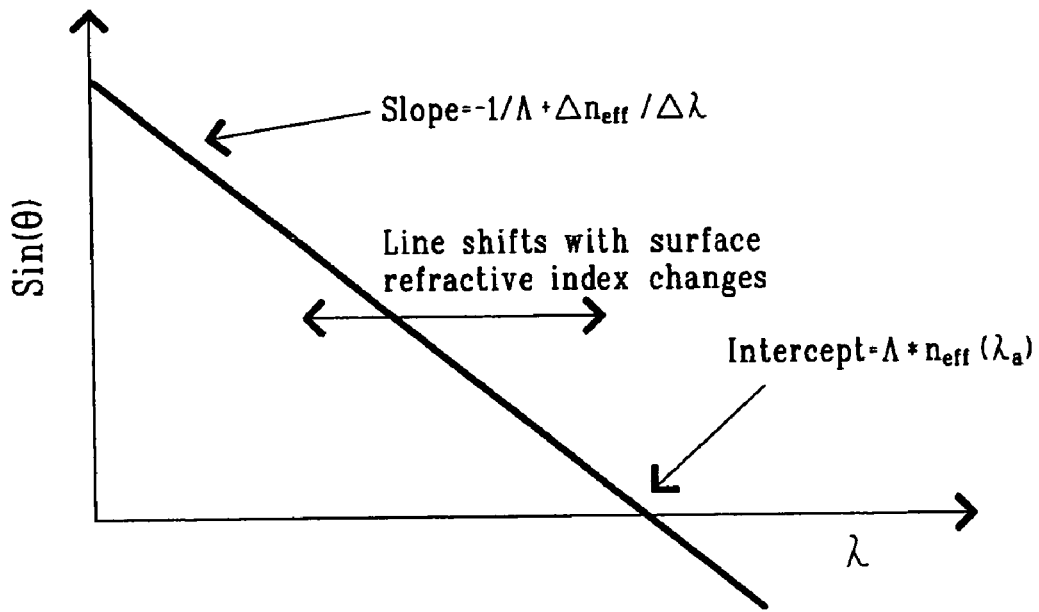
FIGS. 2-4 are graphs used to help describe how the resonant waveguide grating biosensor can be interrogated by the optical reader system in order to determine whether or not a biomolecular binding event occurred on the biosensor.
Figure 3:
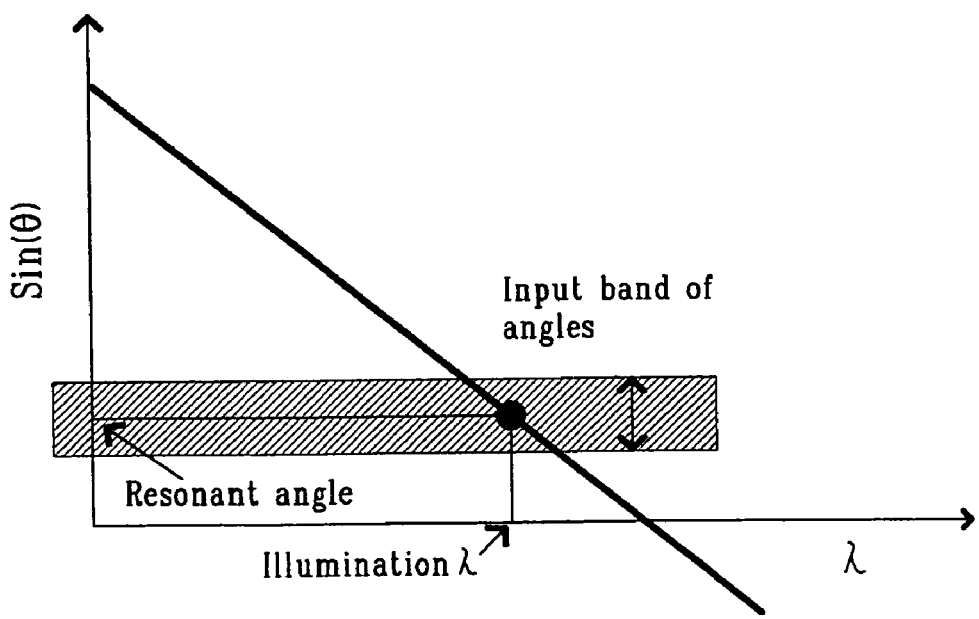
Figure 4:
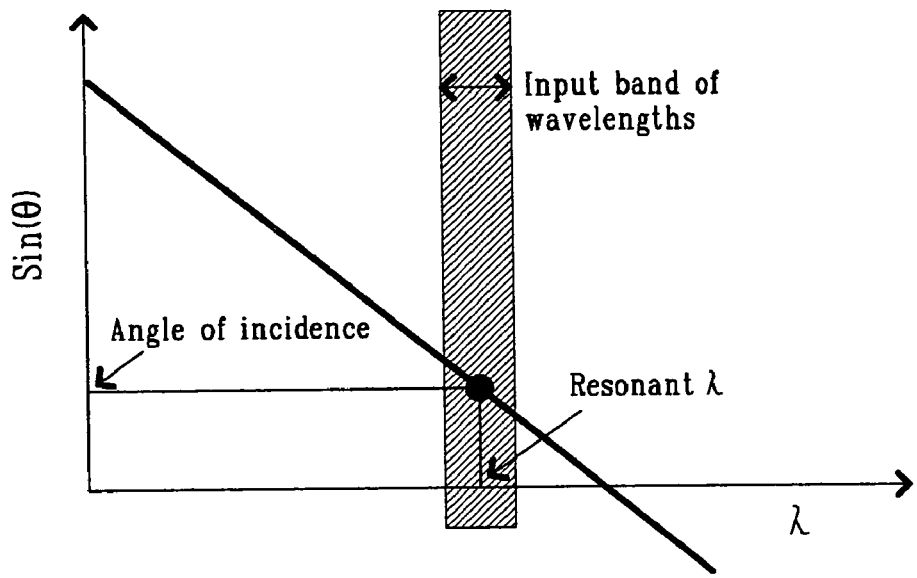

Referring to FIGS. 1-37, there are disclosed several diagrams, photos and graphs which are used to help describe the optical reader system 100 and method 100b of the present invention. As shown in FIGS. 1A and 1B, the optical reader system 100 is preferably used to interrogate a biosensor 102 (e.g., resonant waveguide grating (RWG) biosensor 102, a surface plasmon resonance (SPR) biosensor 102) to determine if a biomolecular binding event occurred on the biosensor 102. The optical reader system 100 includes a light source 106 (e.g., lamp, laser, diode) that outputs (step 102b) an optical beam 104 which is scanned (step 104b) across the biosensor 102. Typically, the biosensor 102 is moved so the optical beam 104 can be scanned across the biosensor 102. Alternatively, the optical beam 104 itself may be scanned with a mirror, galvanometer, electro-optic or acousto-optic scanner or other suitable adjustable optical element, across a stationary biosensor 102. While the optical beam 104 is scanned across the biosensor 102, a detector 108 (e.g., spectrometer, CCD camera or other optical detector) collects (step 106b) an optical beam 112 which is reflected from the biosensor 102. A processor 110 (e.g., DSP 110, computer 110) then processes (step 108b) the collected optical beam 112 to obtain and record (step b) raw spectral data 114 which is a function of a position (and possibly time) on the biosensor 102. Thereafter, the processor 110 analyzes the raw spectral data 114 to create a spatial map of resonant wavelength (peak position) data which indicates if a biomolecular binding event occurred on the biosensor 102.

In other aspects of the present invention, the computer 110 can analyze the raw spectral data 114 to perform a wide range of tasks in addition to detecting a biomolecular binding event on the biosensor 102. For instance, the processor 110 can analyze the raw spectral data 114 to create a spatial map of reflected power that can be used to locate an edge of a grating in the biosensor 102 so that biosensor 102 can be properly re-located after being removed and reinserted into a path of the optical beam 104. And, the processor 110 can analyze the raw spectral data 114 to create a spatial map of reflected power and reflected wavelength which can be used to evaluate the locations, quantities and sizes of defects on the biosensor 102. Moreover, the processor 110 can analyze the raw spectral data 114 to create a spatial map of reflected wavelength data that can be used to ameliorate undesirable effects on changes in measured wavelengths that arise from drifts of the detector 108 and other sources of error including waveguide coating drift, source spectra variations overtime, or bulk index error. More details about the optical reader system 100 and the uses of the raw spectral data 114 are described below after a brief description is provided about the structure of the biosensor 102 and about the different ways the biosensor 102 can be used to detect a biomolecular binding event.

As shown in FIG. 1A, the biosensor 102 includes a thin (~100 nm) layer of material 116 (e.g., waveguide film 116) deposited on a substrate 118 either before or after the fabrication of a diffraction grating 120 which together form a waveguide 122. The diffraction grating 120 is formed within the substrate 118 or waveguide film 116 by embossing, holography, or other methods. The diffraction grating 120 can thereby be located above, below, or even within the waveguide film 116. The waveguide film 116 is preferably made of a metal-oxide based material such as $Ta_2O_5$, $TiO_2$, $TiO_2$—$SiO_2$, $HfO_2$, $ZrO_2$, $Al_2O_3$, $Si_3N_4$, HfON, SiON, scandium oxides or mixtures thereof. As shown, the diffraction grating 120 was formed within a substrate 118 and then the thin waveguide film 116 having a higher refractive index was coated on top of the diffraction grating 120.

The biosensor 102 makes use of changes in the refractive index at the sensor surface that affect the waveguide coupling properties of the optical beam 104 emitted from the light source 106 and the optical beam 112 reflected back into the detector 108 to enable label-free detection of a biological substance 124 (e.g., cell, molecule, protein, drug, chemical compound, nucleic acid, peptide, carbohydrate) on the superstrate 103 (sensing region) of the biosensor 102. The biological substance 124 may be located within a bulk fluid that is deposited on the superstrate 103 (sensing region) of the biosensor 102 and it is the presence of this biological substance 124 that alters the index of refraction at the surface 126 of the biosensor 102. Thus, to detect the biological substance 124, the biosensor 102 needs to be at least probed with an optical beam 104 and then a reflected optical beam 112 received at the detector 108 is analyzed to determine if there are any changes (~1 part per million) in the refractive index caused by the presence of the biological substance 124. In one embodiment, the top surface 126 may be coated with biochemical compounds (not shown) that only allow surface attachment of specific complementary biological substances 124 which enables a biosensor 102 to be created that is both highly sensitive and highly specific. In this way, the optical reader system 100 and biosensor 102 may be used to detect a wide variety of biological substances 124. And, if multiple biosensors 102 are arranged in array an like in a microplate then they may be used to enable high throughput drug or chemical screening studies (see FIG. 5). A more detailed discussion about the structure of the preferred biosensor 102 is provided in the following documents:

U.S. Pat. No. 4,815,843 entitled "Optical Sensor for Selective Detection of Substances and/or for the Detection of Refractive Index Changes in Gaseous, Liquid, Solid and Porous Samples".

K. Tiefenthaler et al. "Integrated Optical Switches and Gas Sensors" Opt. Lett. 10, No. 4, April 1984, pp. 137-139.

The contents of these documents are incorporated by reference herein.

The sensitivity of the biosensor 102 may be best understood by analyzing the structure of the diffraction grating 120 and the waveguide 122. The optical beam 104 shone on the diffraction grating 120 can only be coupled into the waveguide 122 if its wave vector satisfies the following resonant condition as shown in equation no. 1:

$$k_x' = k_x - \kappa \quad [1]$$

where $k_x'$ is the x-component of the incident wave vector, $k_x$ is the guided mode wave vector, and $\kappa$ is the grating vector. The grating vector $\kappa$ is defined as a vector having a direction perpendicular to the lines of the diffraction grating 120 and a magnitude given by $2\pi/\Lambda$ where $\Lambda$ is the grating period (pitch) (see FIG. 1A). This expression may also be written in terms of wavelength $\lambda$ and incident angle $\theta$ as shown in equation no. 2:

$$\frac{2\pi n_{inc}}{\lambda} \sin\theta = \frac{2\pi n_{eff}}{\lambda} - \frac{2\pi}{\Lambda} \quad [2]$$

Where $\theta$ is the angle of incidence of the optical beam 104, $n_{inc}$ is the index of refraction of the incident medium, $\lambda$ is the wavelength of the optical beam 104, and $n_{eff}$ is the effective index of refraction of the waveguide 122. The effective index of the waveguide 122 is a weighted average of the indices of refraction that the optical waveguide mode field "sees" as it propagates through the waveguide 122. The optical waveguide mode preferably has a spatial extent that is much wider than the waveguide 122 itself, the extent depending on the refractive index of the substrate 118. In particular, the optical waveguide mode has an evanescent wave/tail that extends into the superstrate 103 (sensing region) which "sees" any surface changes created when the biological substance 124 approaches or comes in contact with the top surface 126 of the biosensor 102.

The previous expression shown in equation no. 2 may be rewritten in the more convenient form shown in equation no. 3:

$$\sin\theta = n_{eff} - \frac{\lambda}{\Lambda} \quad [3]$$

which is the equation of a line where $\sin\theta$ being the y axis, $\lambda$ being the x-axis, $\Delta n_{eff}$ the x-intercept, and $-1/\Lambda$ the slope. To obtain equation no. 3, $n_{inc}$ has been set to 1 so that it could be removed from this expression. This approximation is used since air (n~1.0003) is the most common incident medium. This relation is pictured in the graph shown in FIG. 2. When a biological substance 124 binds to the surface 126, the effective index of the waveguide 122 is altered which leads to the shifting the resonant wavelength or resonant angle of the biosensor 102. This shifting can be seen as a shift of the x-intercept in the line shown in FIG. 2.

The resonant condition (e.g., resonant wavelength or resonant angle) of such a biosensor 102 may be interrogated to determine refractive index changes by observing the optical beam 112 reflected from the biosensor 102 (see FIG. 1A). There are two different modes of operation for monitoring refractive index changes from such a resonant waveguide grating biosensor—angular interrogation or spectral interrogation. In angular interrogation, a nominally single wavelength optical beam 104 is focused to create a range of illumination angles and directed into the biosensor 102. The reflected optical beam 112 is monitored with a CCD camera or other optical detector 108. By monitoring the position of the resonant angle reflected by the biosensor 102, one can monitor binding or refractive index changes on or near the surface 126 of the biosensor 102. The angular interrogation concept is graphically represented in the graph shown in FIG. 3. In spectral interrogation, a nominally collimated, broadband optical beam 104 is sent into the biosensor 102 and the reflected optical beam 112 is collected and monitored with a spectrometer 108 (for example). By observing the spectral location of the resonant wavelength (peak), one can monitor binding or refractive index changes on or near the surface 126 of the biosensor 102. The spectral interrogation concept is graphically represented in the graph shown in FIG. 4. In the present invention, the focus of the description is on the method of spectral interrogation even though the present invention can utilize both interrogation methods.

Referring again to FIG. 1A, the spatially scanned optical reader system 100 is shown where an optical beam 104 strikes the biosensor 102 and the reflected optical beam 112 is collected and interrogated by the spectral method. As can be seen, the optical beam 104 is translated across the moving biosensor 102, and spectral data 114 is recorded as a function of position on the biosensor 102. The optical beam 104 may be swept in a line, raster scanned across two dimensions of the biosensor 102, or made to move in an arbitrary pattern across the biosensor 102. The raw spectral data 114 may also be obtained and recorded as a function of time by performing repetitive scans across the biosensor 102. Once the raw spectral data 114 is obtained as a function of position and possibly time, it may be processed to produce a spatial map of resonant wavelength data (peak position) that indicates whether or not a biological binding event occurred on the biosensor 102. In this way, the surface refractive index of the biosensor 102 can be spatially and temporally mapped. Of course, for this to work the optical beam 104 needs to be smaller than the biosensor 102. As such, a focusing optic may be needed to alter the shape and size of the optical beam 104 so that it is smaller than the biosensor 102 (see focusing lens 514 in FIG. 5).

Figure 5:
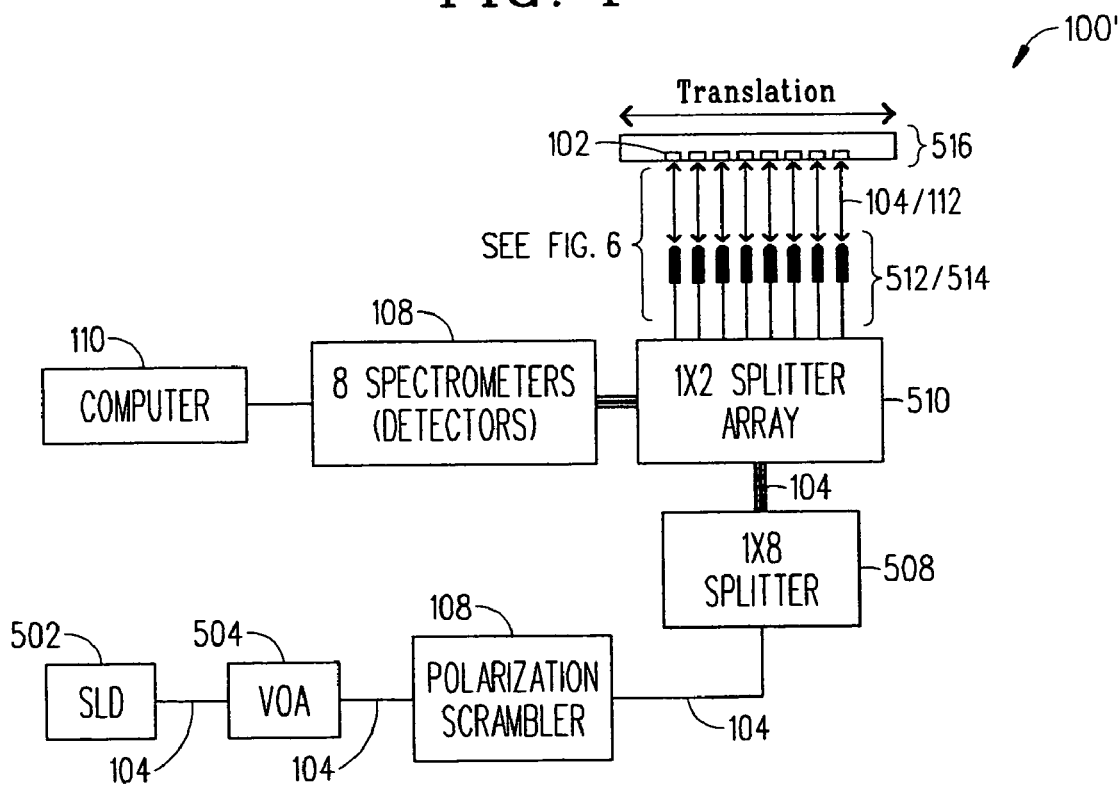
FIGS. 5 and 6 are block diagrams used to describe how the optical reader system can be configured so it can interrogate multiple biosensors that are located in a microplate in accordance with another embodiment of the present invention.
Figure 6:
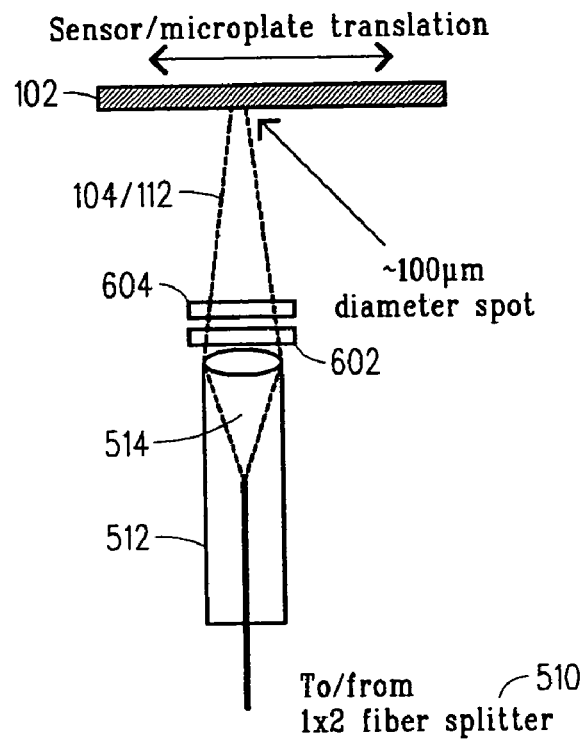

Referring to FIG. 5, there is shown a schematic of an embodiment of an optical reader system 100' which is configured so it can interrogate multiple biosensors 102 that are located in a microplate 516. As shown, a super-luminescent diode (SLD) 502 emits an optical beam 104 that is sent through a variable optical attenuator (VOA) 504 and a polarization scrambler 506 and is then split into 8 channels using a series of two splitters 508 and 510. The optical beams 104 are then sent through eight fibers 512 and eight focusing lenses 514 which create a series of nominally 100 µm diameter optical beams 104. These spots illuminate from below one column (8 wells) of a microplate 516 where each well contains an ~3 mm square RWG biosensor 102. FIG. 6 shows a schematic of the optics used to create each interrogating beam 104. As can be seen, the single mode fiber 512 and pigtailed lens 514 forms the nominally 100 µm diameter optical beam 104 on one of the RWG biosensors 102. The reflected light 112 is collected by the same fiber 512 and lens 514 and passed back into the fiber splitters 510 and 508 and then routed to a series of eight spectrometers 108 which are read out by a processor 110 (see FIG. 5). A combination of a linear polarizer 602 and a quarter wave plate 604 can be placed near the end of the fiber 512 to reject Fresnel and other parasitic reflections while passing the resonantly reflected light 112. As shown, the microplate 516 is moved across the optical reader system 100' and the raw spectral data 114 in the reflected optical beam 112 is recorded as a function of plate (sensor) position.

As mentioned above, the raw spectral data 114 can be analyzed by the processor 110 to enable a wide range of tasks to be performed. For instance, the raw data 114 can be used to: (1) detect biomolecular binding event(s); (2) characterize the biosensor 102; (3) register the biosensor 102; and (4) mitigate optical system artifacts. Each of these tasks is described in greater detail below with respect to FIGS. 7-36.

Detect Biomolecular Binding Event(s)

How the optical reader system 100 and 100' can use a scanned optical beam 104 to interrogate one or more biosensors 104 has been described above with respect to FIGS. 1-6. However, a problem that can affect the accuracy of any optical reader system occurs when there is a change in the resonant wavelength (or angle) which is caused by things like the environment rather than the specific binding event of interest. In short, anything that changes the refractive index of the biosensor 102 may cause false or spurious signals. For example, the things that can affect the biosensor 102 include temperature changes, the introduction of fluids with different bulk refractive indices, pressure changes and non-specific binding of molecules to the sensor's surface 126. To combat this problem, optical reader systems have made use of a "reference" biosensor and a "sample" biosensor, where the reference biosensor is exposed to similar environmental conditions and fluids as the sample biosensor, but whose surface is prepared such that no biochemical binding takes place. Reference is made to the following documents for a more detailed discussion about how two biosensors have been used in attempt to solve this problem:

- J. Dubendorfer et al. "Sensing and Reference Pads for Integrated Optical Immunosensors" J. Biom. Optics, 2(4), 391-400 (October 1997).
- M. Wiki et al. "Wavelength-Interrogated Optical Sensor for Biochemical Applications," Optics Letters 25, No. 7, 463-465 (2000).
- K. Cottier et al. "Label-Free Highly Sensitive Detection of (Small) Molecules by Wavelength Interrogation of Integrated Optical Chips" Sensors and Actuators B 91 (2003) 241-251.
- K. Tiefenthaler et al. "Sensitivity of Grating Couplers as Integrated-Optical Chemical Sensors" J. Opt. Soc. Am. B 6, No. 2, February 1989, pp. 209-220.
- W. Lukosz et al. "Integrated Optical Chemical and Direct Biochemical Sensors" Sensors and Actuators B 29, 1995, pp. 37-50.
- M. Wiki et al. "Novel Integrated Optical Sensor Based on a Grating Coupler Triplet," Biosensors and Bioelectronics 13 (1998) 1181-1185.

The contents of these documents are incorporated by reference herein.

However such referencing techniques are imperfect, since any two biosensors 102 may see different signals due to pipetting errors, temperature gradients, or other well-to-well (sensor-to-sensor) changes. An improved strategy has been developed in which a sample (binding) region and reference (non-binding) region are formed on the same biosensor 102. How this can be done was described in detail in a related U.S. patent application Ser. No. 11/027,509 entitled "Method for Creating a Reference Region and a Sample Region on a Biosensor and the Resulting Biosensor".

Figure 7:
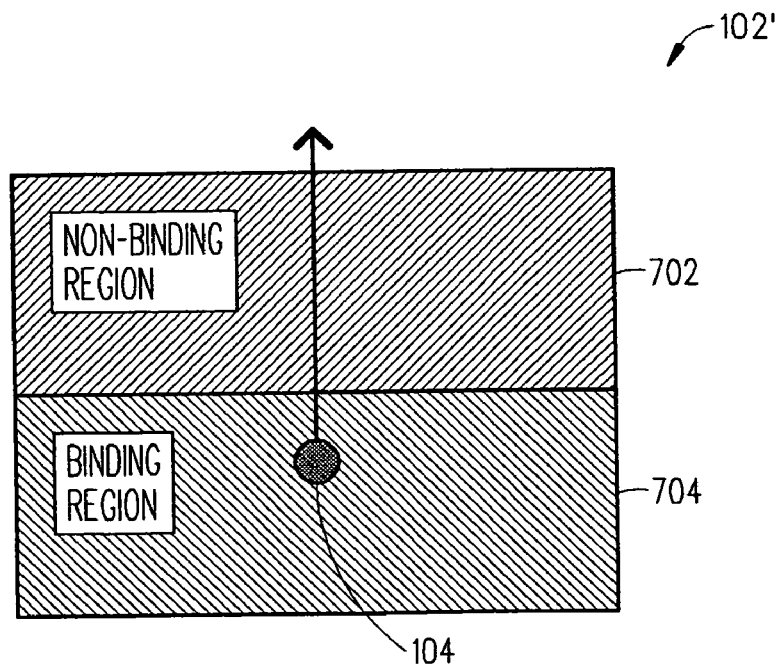
FIGS. 7-15 are graphs and diagrams that are used to illustrate the results of several experiments which where conducted to show how the raw spectral data obtained from the optical reader system can be used to detect a biomolecular binding event in accordance with the present invention.

FIG. 7 shows an example of this type of biosensor 102' where the reference (non-binding) region 702 is designed to respond to the same local environmental changes, but not to the biochemical binding event of interest that occurs in the sample (binding) region 704. If the biosensor 102' is designed so that the non-binding region 702 and binding region 704 are in close proximity to one another, then one may remove the environmental effects from the signal by subtracting the non-binding region's wavelength change from the binding region's wavelength change. However, this leads to the problem of how to interrogate the closely spaced non-binding region 702 and binding region 704. This problem can be solved with the optical reader system 100 and 100' of the present invention where the optical beam 104 is scanned across both the non-binding and binding regions 702 and 704 as shown in FIG. 7. The traditional optical reader systems would have difficulty in solving this problem since they do not use a scanned optical beam 104.

Following are descriptions about the results of several experiments that were conducted to show how one can better detect a biomolecular binding event in the presence of undesired environmental noise using the optical reader system 100' and microplate 516 shown in FIGS. 5 and 6 and the biosensor 102' shown in FIG. 7.

Figure 8:
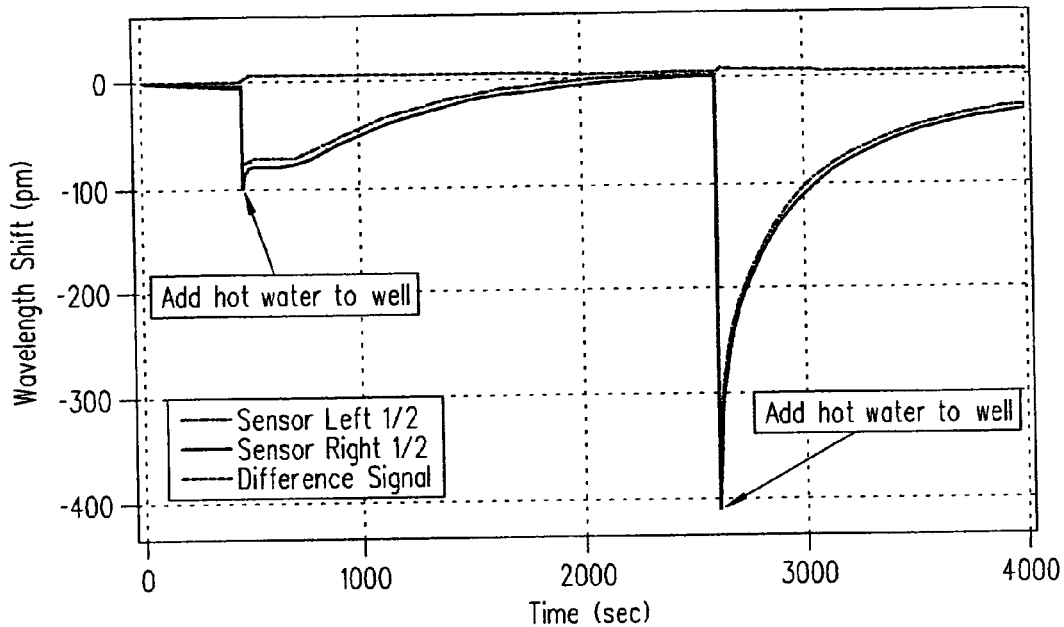

FIG. 8 is a graph that shows the results of an experiment in which the wavelengths of each half (left and right) of a RWG sensor 102' were tracked as a function of time while the temperature of the well, containing water, was changed by adding hot water to the well. In this experiment, there was a ~5° C. temperature change upon the first addition of water, and a ~20° C. change on the second addition of water to the well. As can be seen, each half of the biosensor 102' responded similarly to the temperature perturbation, so that, when subtracted, the effect of temperature is removed.

Figure 9:
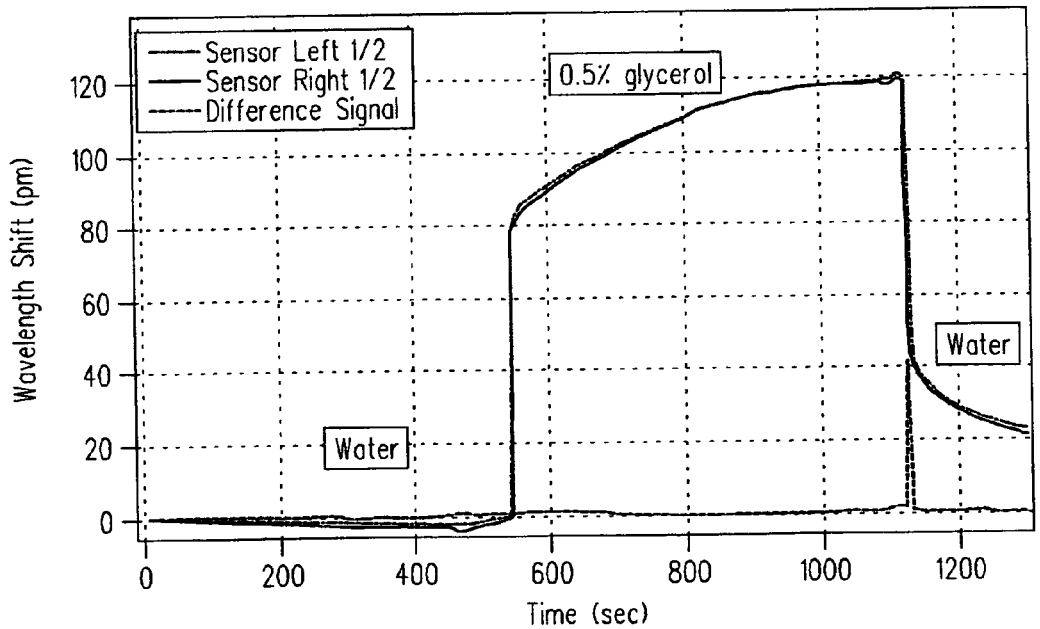

FIG. 9 is a graph that shows the results of an experiment that is similar to the previous experiment except where the water was replaced by a solution of 0.5% glycerol. Here the refractive index of the solution changed because of the glycerol concentration, and each half of the biosensor 102' exhibited a wavelength change. However, once again when the wavelength changes of each half of the biosensor 102' are subtracted it can be seen that the impact of the bulk refractive index change is removed.

Figure 10:
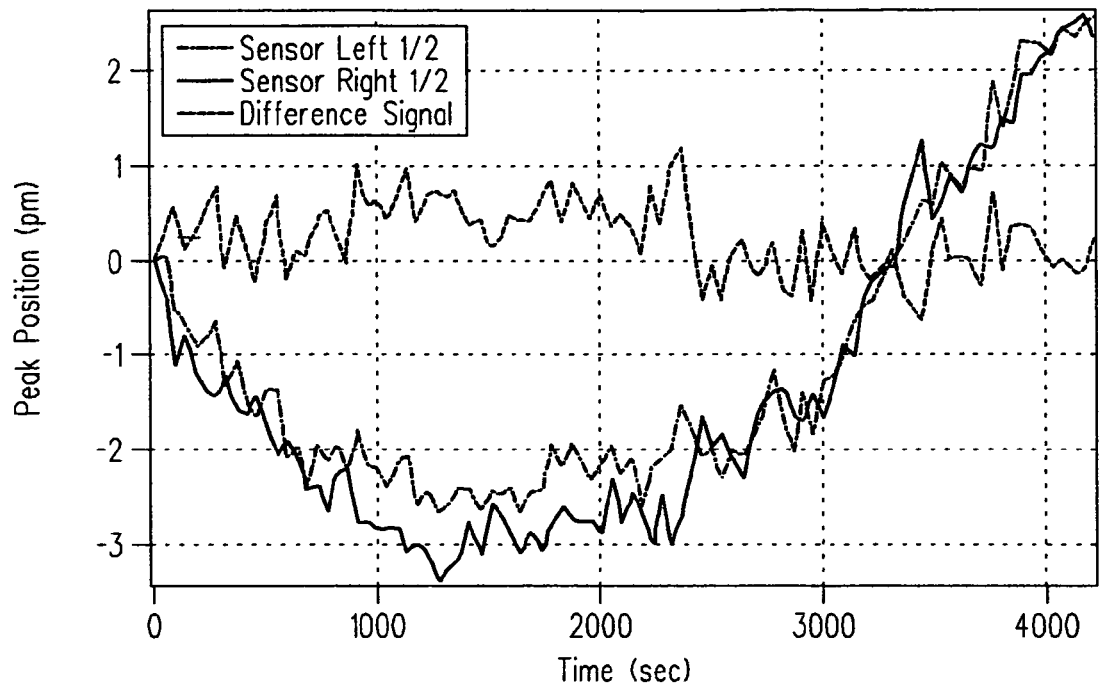

FIG. 10 is a graph that shows the results of an experiment where a RWG biosensor 102' covered with water was monitored as a function of time by the optical reader system 100'. The graph shows the wavelengths of each of the halves of the biosensor 102, and also shows the signal difference between each of those wavelengths. As can be seen, the slowly changing environmental effects are removed after the subtraction of the wavelengths associated with each half of the biosensor 102.

FIGS. 11-14 are used to show the results of experiments that were conducted using the optical reader system 100' and well plates 516 containing 3 mm square RWG biosensors 102' which were prepared by blocking half of the sensor surface with O,O'-Bis(2-aminorropvl)polyethyleneglycol 1900 (PEG). The blocking agent was applied using a pin-printer, and details on how this can be done are provided in the aforementioned U.S. patent application Ser. No. 11/027,509. The biosensor 102' that was created was one where target molecules and subsequent analyte molecules would bind only to the unblocked portion (sample region 704).

Figure 11:
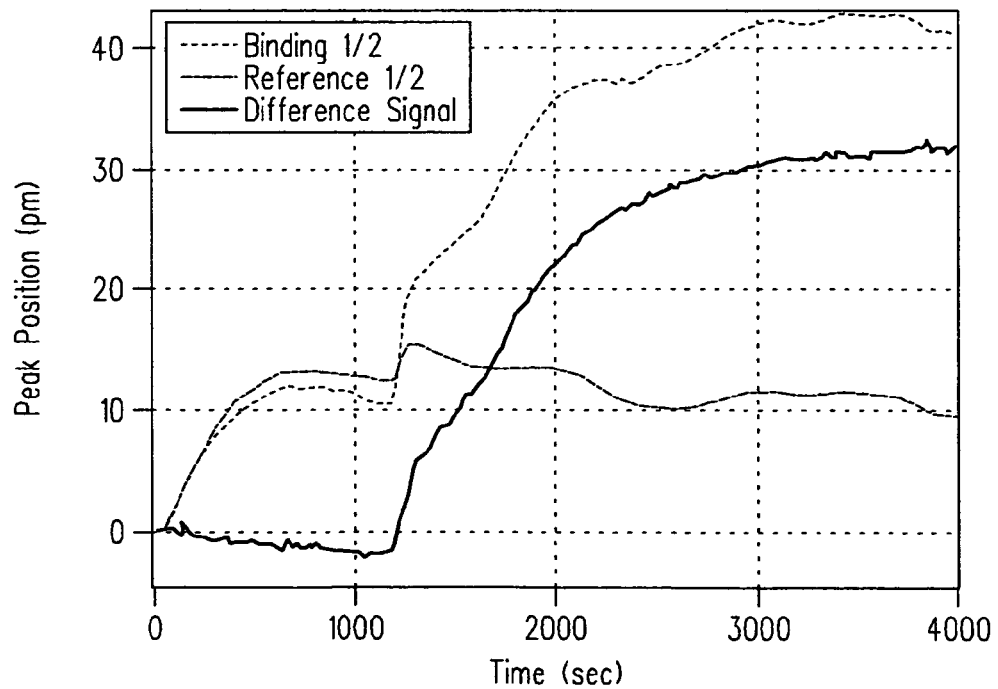

FIG. 11 is a graph that shows the results of an assay where streptavidin (SA) was immobilized on the binding region. 704 of the biosensor 102', and then a solution containing fluorescein-biotin was added to the wells. As can be seen, the difference signal displays the binding process itself without showing many of the environmental drifts present in the signals from the reference region 702 and the binding region 704.

Figure 12:
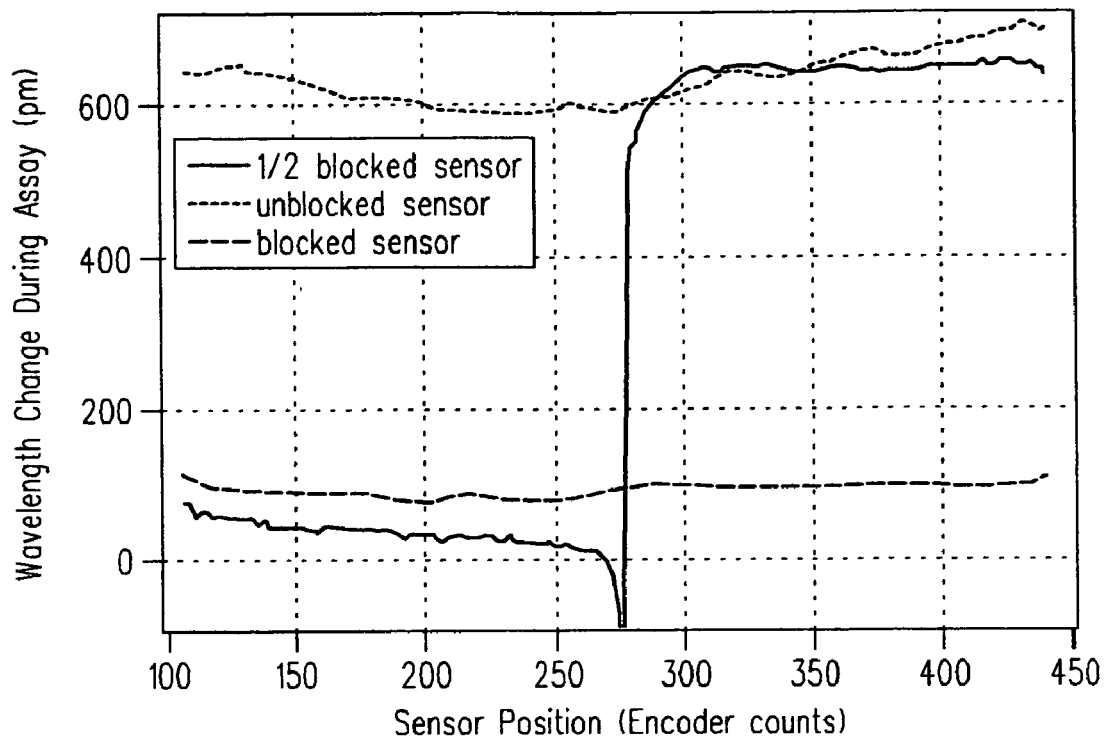

FIG. 12 is a graph that shows the results of an assay where several intra-well referenced biosensors 102' were interrogated by the optical reader system 100'. In this assay, biotin-labeled bovine serum albumin (BSA) was immobilized on some but not all of the binding regions 704 of the biosensors 102'. A solution of streptavidin (SA) was introduced into each well and the amount of wavelength shift during this binding assay was recorded as a function of position across the sensor. In FIG. 12, one trace shows a biosensor 102' with no blocking agent, another trace shows a biosensor 102' that was entirely blocked, and the third trace shows a biosensor 102' that was half blocked. As can be seen, the response of the half blocked biosensor 102' in the region without the PEG blocker was the same as the unblocked biosensor 102'. The blocked (non-binding) regions 702 of the half blocked biosensor 102' did exhibit a small amount of wavelength change, which may be attributed to non-specific binding of the SA. However, this non-specific binding is nearly identical on both regions 702 and 704 of the half blocked biosensor 102', and hence may be referenced out when the two signals are subtracted.

Figure 13:
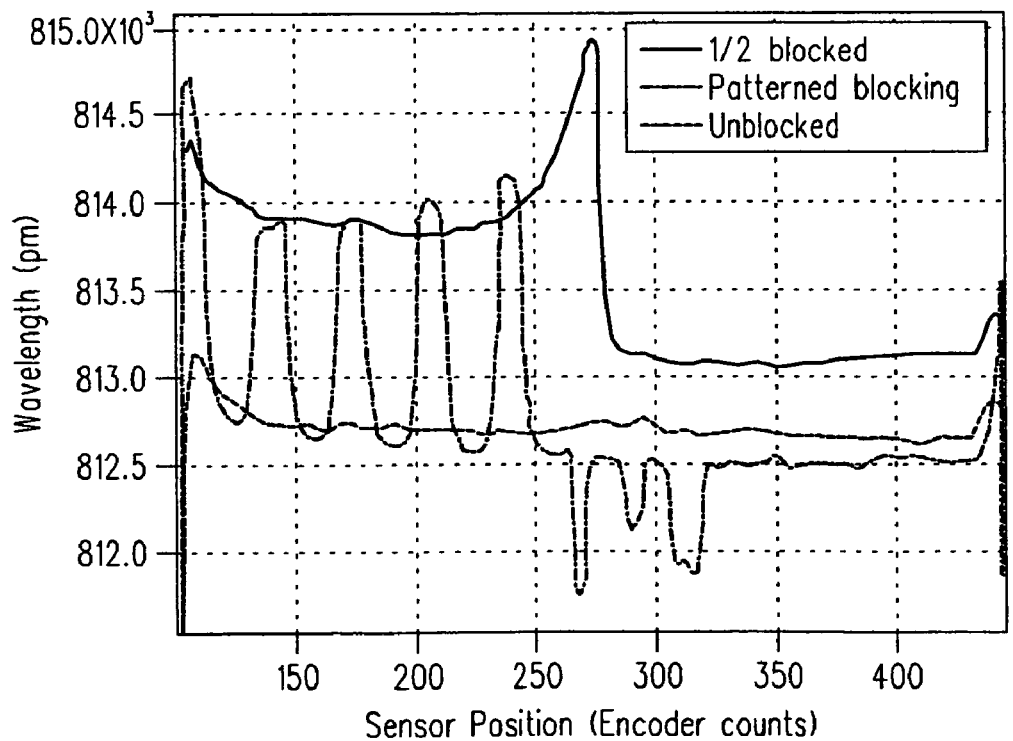

FIG. 13 is a graph that shows the high spatial frequency patterning of non-binding and binding regions 702 and 704 of a biosensor 102'. The PEG blocking agent used created a sufficiently thick layer so as to cause a resonant wavelength shift of ~1 nm in the region 702 where it was present. The optical reader system 100' produced transitions between blocked and unblocked regions 702 and 704 that were sharp and well defined, with each region being approximately 150 μm wide.

Figure 14:
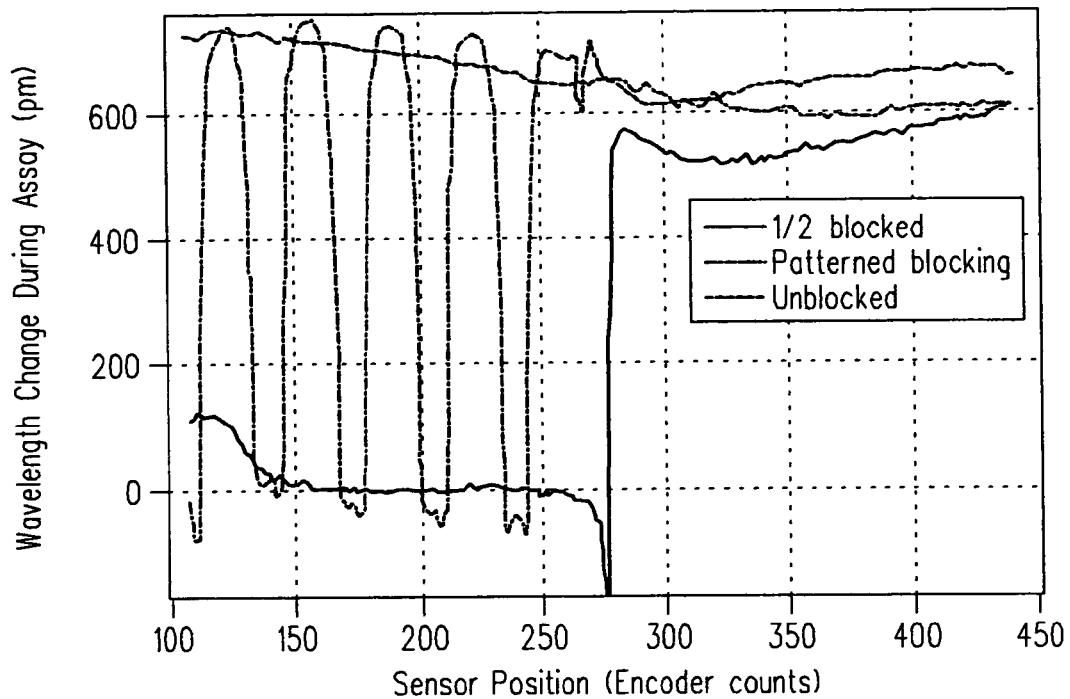

FIG. 14 is a graph that shows the net wavelength change that occurred during the assay associated with FIG. 13. As can be seen, the same reference regions 702 that were blocked exhibited little wavelength change, whereas the sample regions 704 that were unblocked exhibited binding signals. The use of such a high spatial frequency pattern can be used to reject any perturbations that vary rapidly as a function of position. These include effects such as large temperature gradients, sensitivity variations across the biosensor 102', and binding variations across the biosensor 102'.

Figures 15A, 15B:
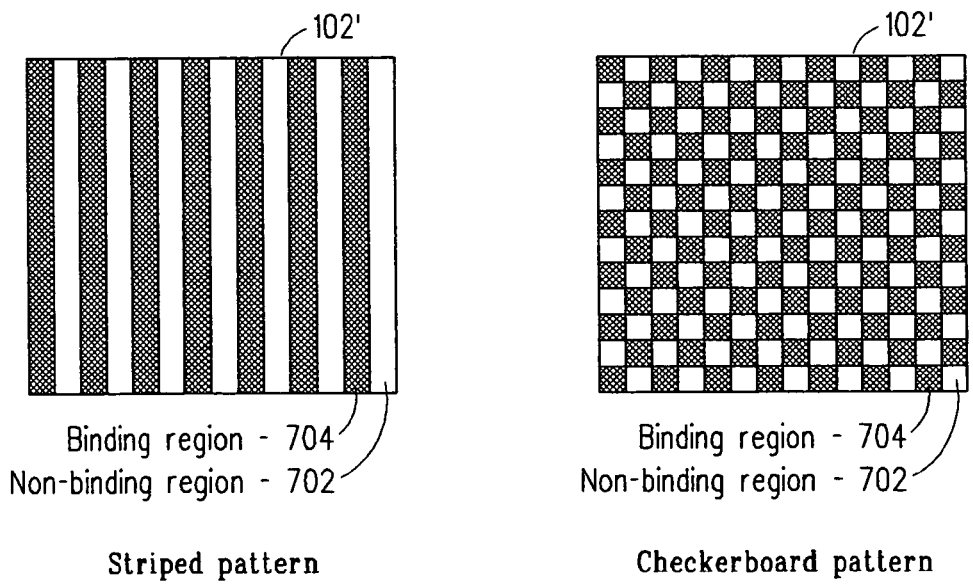

FIGS. 15A and 15B are two diagrams that show different examples of patterning techniques that may be used on an intra-well referenced biosensor 102'. These patterning techniques may be employed with binding/non-binding areas only, or they may be employed in situations where different target molecules are immobilized in each distinct binding region 704, which allows the multiplexing of assays with a single RWG biosensor 102'. This technique is described in more detail in a related U.S. patent application Ser. No. 11/027,509 entitled "Method for Creating a Reference Region and a Sample Region on a Biosensor and the Resulting Biosensor".

Characterization of Biosensor 102

As briefly mentioned above, the optical reader system 100 can use a scanned optical beam 104 and the resulting raw spectral data 114 to perform a variety of tasks like create a spatial map of sensor resonant wavelength, reflectivity, peak width, local angle, wavelength interrogation slope (WIS), and other parameters. Some of these spatial maps can be used to characterize a biosensor 102 and 102'. For instance, an example of a spatial map of reflectivity that was obtained from a group of biosensors 102 using small optical beams 104 (~100 micron diameter) is shown in the graph of FIG. 16.

Figure 16:
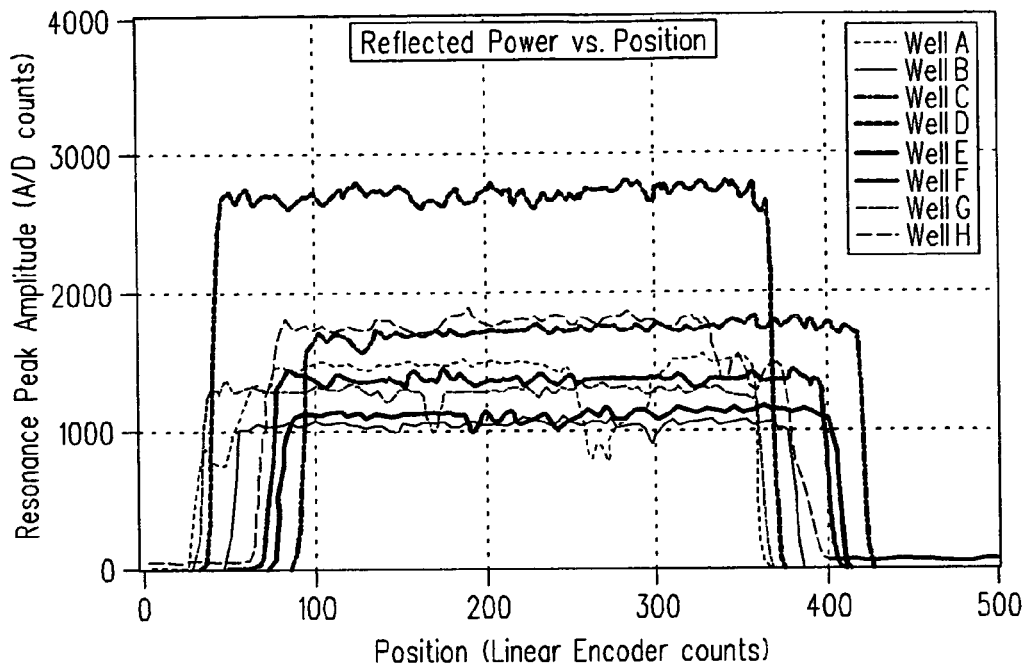
FIGS. 16-17 are graphs that are used to illustrate the results of an experiment which was conducted to show how the raw spectral data obtained from the optical reader system can be used to characterize a biosensor in accordance with the present invention.
Figure 17:
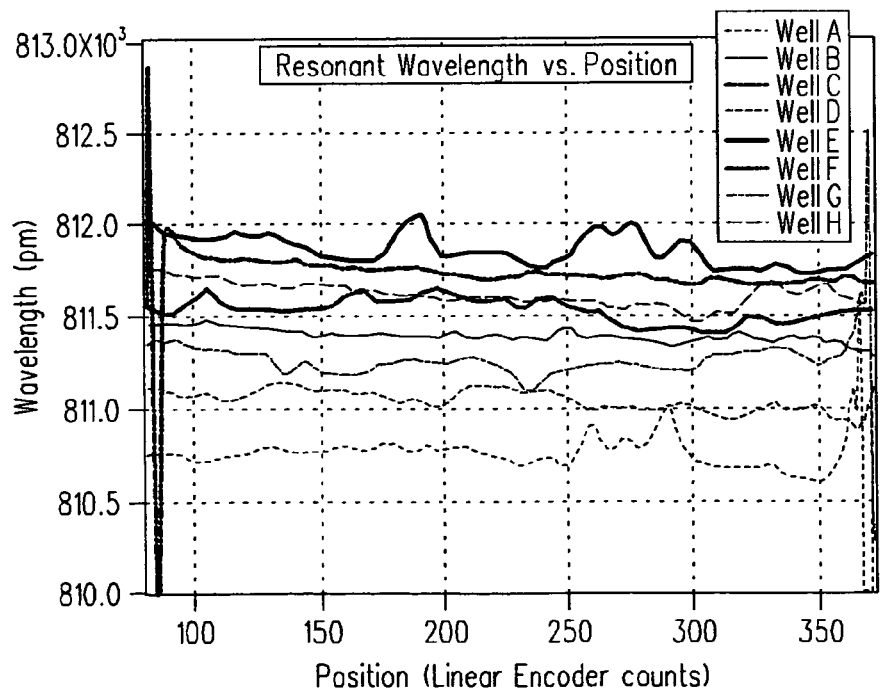
Figure 18:
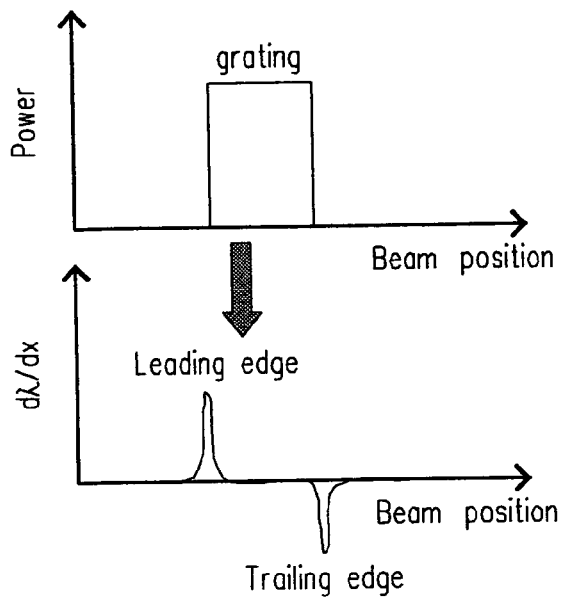
FIGS. 18-20 are graphs and diagrams that are used to illustrate the results of an experiment which was conducted to show how the raw spectral data obtained from the optical reader system can be used to register the position of a biosensor in accordance with the present invention.

And, FIG. 17 is a graph that shows the resonant wavelength data from the same scan used in FIG. 16. In these graphs, it can be seen how reflectivity and wavelength varies as a function of position, and one may use this data to characterize the biosensor 102' by evaluating the coating uniformity, the locations, the quantities and sizes of defects. This spatial information can also be used to exclude regions with obvious defects from use in calculations. In addition, one may use this scanned data and take the average of the wavelength across specified regions of a biosensor 102 to reduce or ameliorate the effects of spatial non-uniformities.

Register the Biosensor 102

The optical reader system 100 can also use a scanned optical beam 104 and the resulting raw spectral data 114 to create a spatial map of reflected power that enables one to precisely locate the edge of the biosensor's gratings 120 (or similar fiducial markings). One can obtain this information by taking the derivative of the power vs. position data and then using the minimum and maximum derivative values to locate the edges of the biosensor 102 as is shown in the graph illustrated in FIG. 18. An advantage of knowing this information is that it enables one to properly re-locate or "register" a biosensor 102 after it is removed and reinserted into the optical path 104. Such registration can be critical as the observed resonant wavelength can vary rapidly with position. In addition this is important because the resonance wavelength is a function of the position of the interrogating beam 104 over the grating 120. So, when the sensor plate 102 is removed from and re-inserted into the reader 100, one can generate some measurement errors because the interrogation is at a slightly different area of the grating 120. So, being able to register the position of the sensor 102 is an important aspect for high throughput readers 100.

Figure 19:
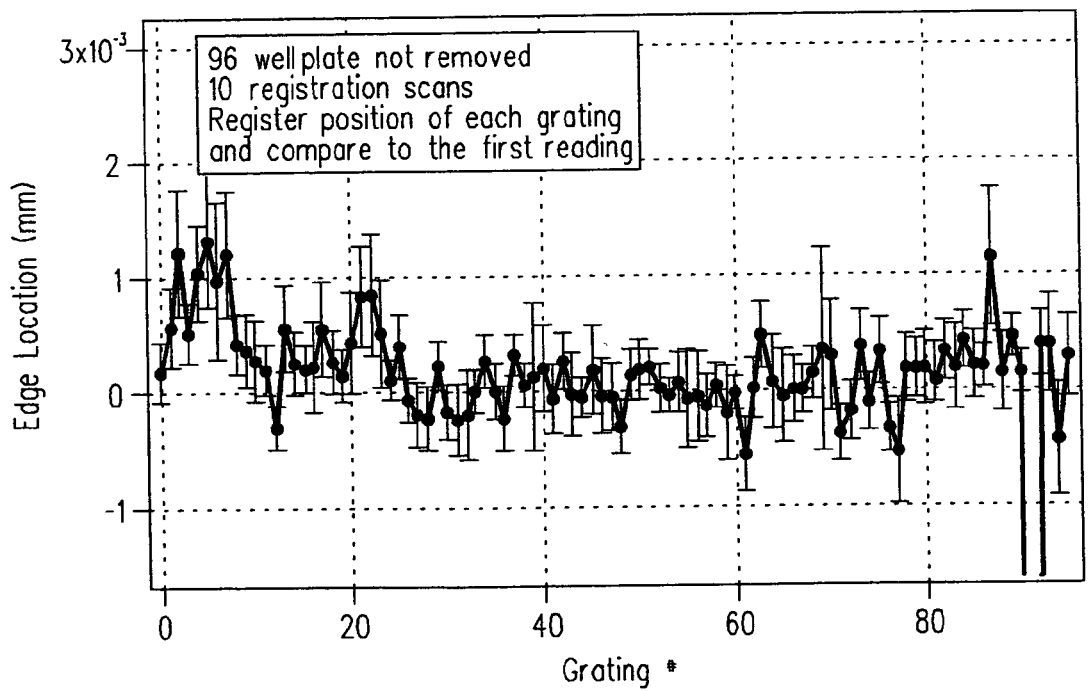
Figure 20:
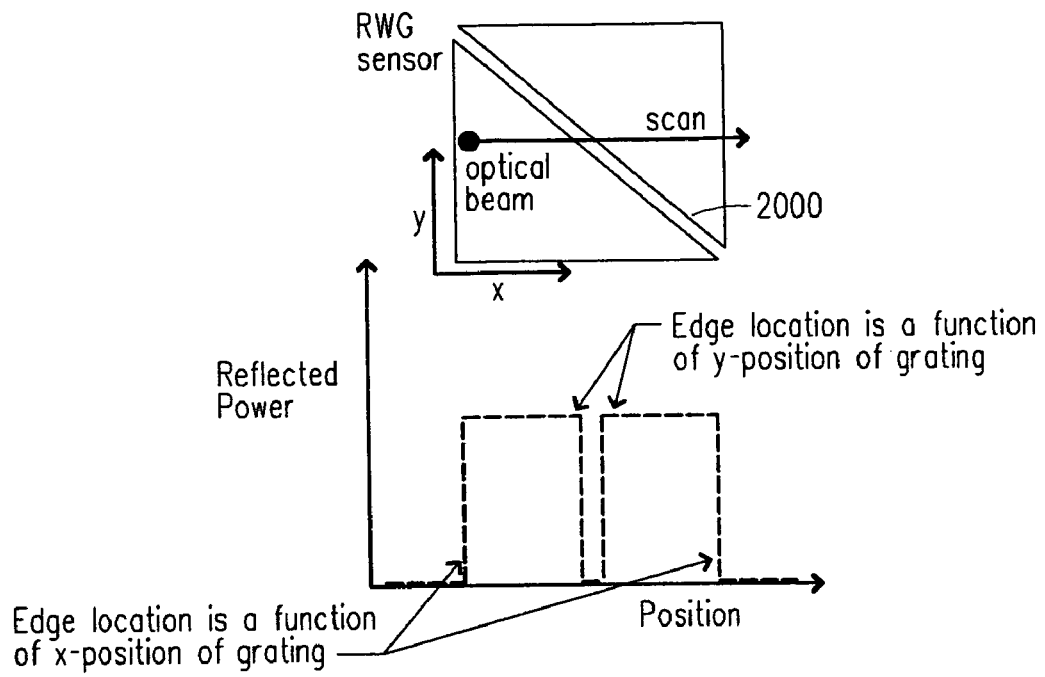

The results of several experiments where the edges of biosensor's gratings 120 were located from such power vs. position data are shown in the graph of FIG. 19. This edge detection technique can be used to register the position of each biosensor 102 to <1 μm. In an alternative embodiment, one may also use specifically designed fiducial markings to refine this registration technique. An example of such a design is shown in FIG. 20 where a diagonal cut 2000 was made across the biosensor 102. The diagonal cut 2000 allows one to estimate both the x and y location of the biosensor 102 with a 1-dimensional beam scan. The rising edge of a power vs. position trace is used to determine the x-position and the difference between the rising and falling edges is used to determine the y-position.

Mitigate Optical System Effects

A second problem associated with repositioning the sensor plate 102 is the angular dependence of the resonance wavelength. Although single mode fibers can be used which should, at first order, be angularly insensitive, some angular dependence can be observed which depends on the lens aberration and on the position of the beam over the grating 120. So, to minimize this error contribution, the same lens should be used for interrogating both the reference and the measurement channels. Also, by scanning the sensor length, one can average the contribution associated with the sensor non-homogeneity so that one can get very repeatable angular sensitivity curves.

Figure 21:
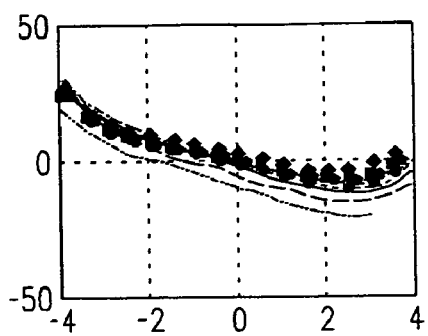
Figure 21:
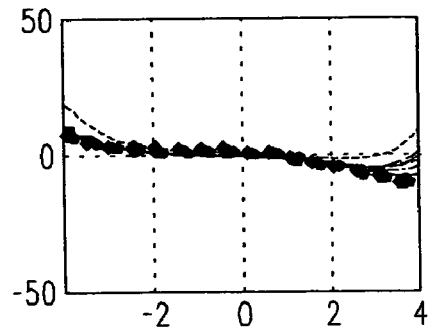
Figure 21:
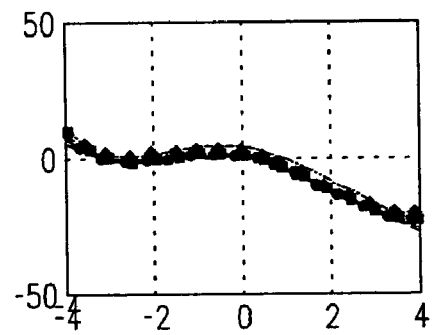
Figure 21:
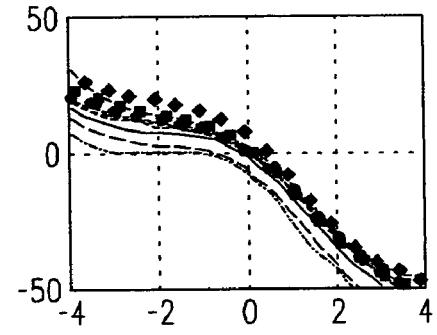
Figure 21:
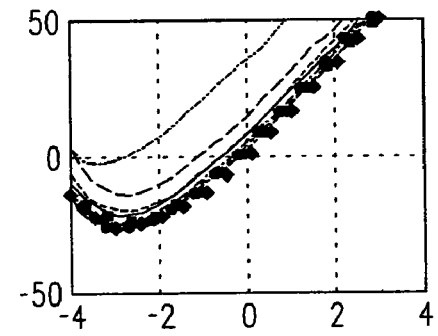
Figure 21:
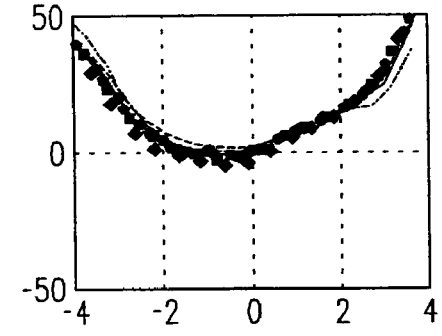
Figure 21:
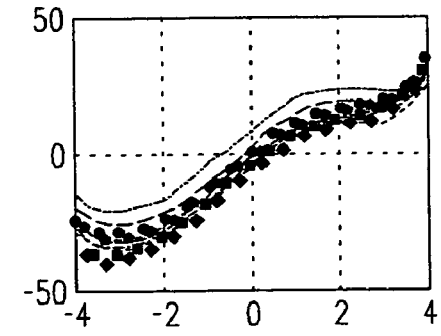
Figure 21:
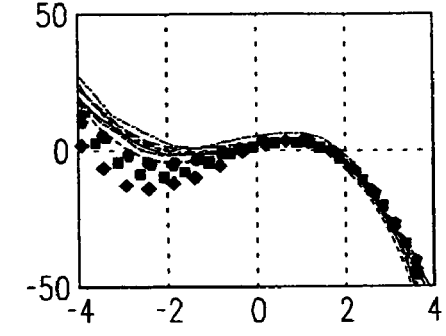

FIG. 21 is a series of plots that show the results of an experiment where a 96 well microplate, with each well containing a RWG biosensor 102, was scanned at a varying set of incident beam angles. Each plot shows a family of 12 curves that were associated with the 12 biosensors 102 of one row in the microplate 516 that were scanned at a variety of angles by the fibers/lens array 512/514. For each curve, the resonance wavelength was calculated as the average of the wavelength measured during the scan of every single sensor 102. As can be seen, the plots clearly indicate that the wavelength change with angle is a function of the optic 514 used, which is common for all biosensors within a given row, and not the biosensor 102 being illuminated. Thus, if the binding and reference regions 702 and 704 of a biosensor 102' are illuminated with the same optic 514, then they will see similar changes if the angle is altered.

Figure 22:
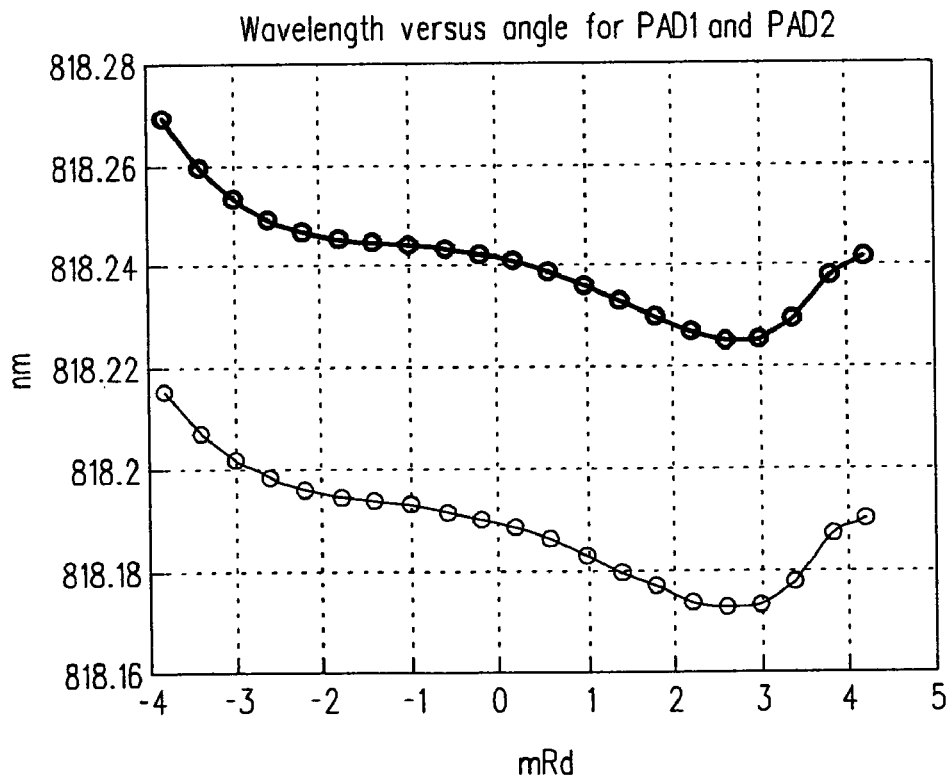
FIGS. 21-23 are graphs that are used to illustrate the results of an experiment which was conducted to show how the raw spectral data obtained from the optical reader system can be used to minimize angular dependent effects of the optical reader system in accordance with the present invention.

FIG. 22 is a graph that shows the results of an experiment where the average wavelength was tracked on each half of one RWG biosensor 102 as that biosensor 102 was tilted. Again, here, the wavelength was averaged over the scan. As can be seen, by subtracting the wavelength changes in each of the reference and binding regions 702 and 704, the net change from angular tilts may be removed.

Figure 23:
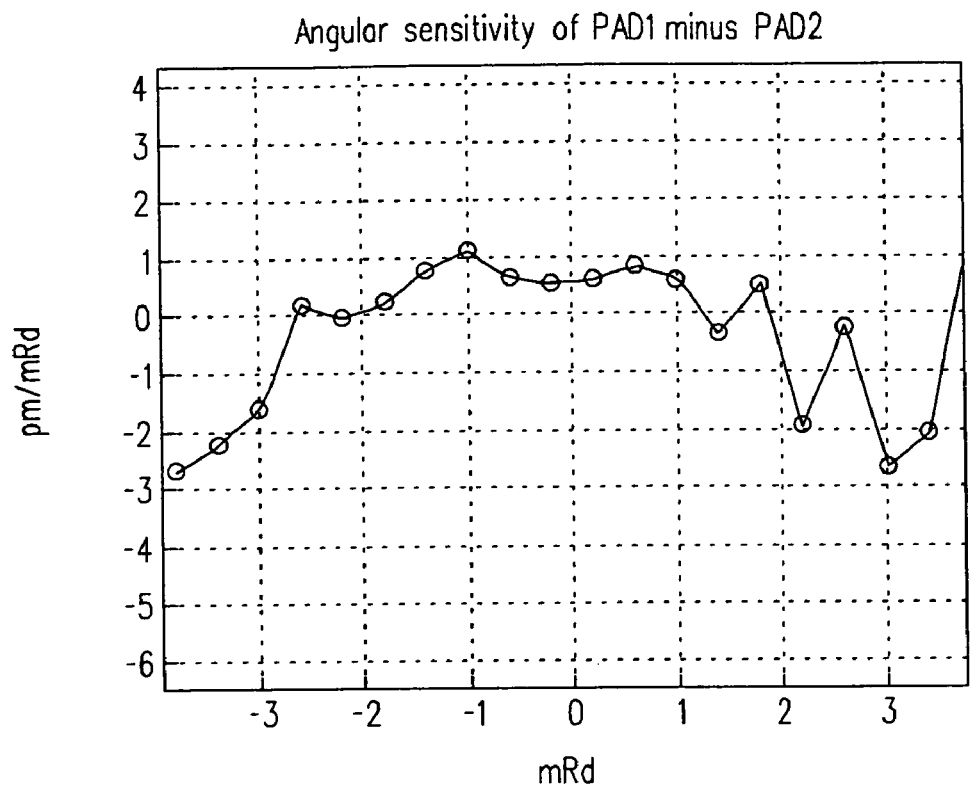

FIG. 23 is a graph that shows the angular sensitivity (in pm/mRad) of this system when the binding and reference signals are subtracted. Angular tilts and misalignment can easily occur if a biosensor 102' is removed and reinserted into the optical reader system 100 and 100'. As such, the mitigation of the impact of angular changes on RWG signal is important for an optical reader system.

Additional Experiment

Following is a description about another experiment that was performed to evaluate the capabilities of the scanned optical reader system 100. Basically, this experiment was performed to determine if there was an advantage of using small interrogating beam sizes and scanning methods to reduce the angular and lateral sensitivities of the measurements.

Two different instrument configurations were analyzed and are referred hereinafter as static configuration and dynamic configuration. In the static configuration, the reference and the measurement areas of the same biosensor 102 were sequentially interrogated by an optical reader system that did not scan the optical beam 104 across the biosensor 102. And, in the dynamic configuration, the reference and the measurement areas of the same biosensor 102 were interrogated by an optical reader system 100 that continuously scanned an optical beam 104 over grating sub-areas called "pads" on the biosensors 102. In the dynamic condition, the resonance wavelength is calculated as the average over the 'pad' length. The biosensors 102 in this experiment used a waveguide made from $Nb_2O_5$.

Figure 24:
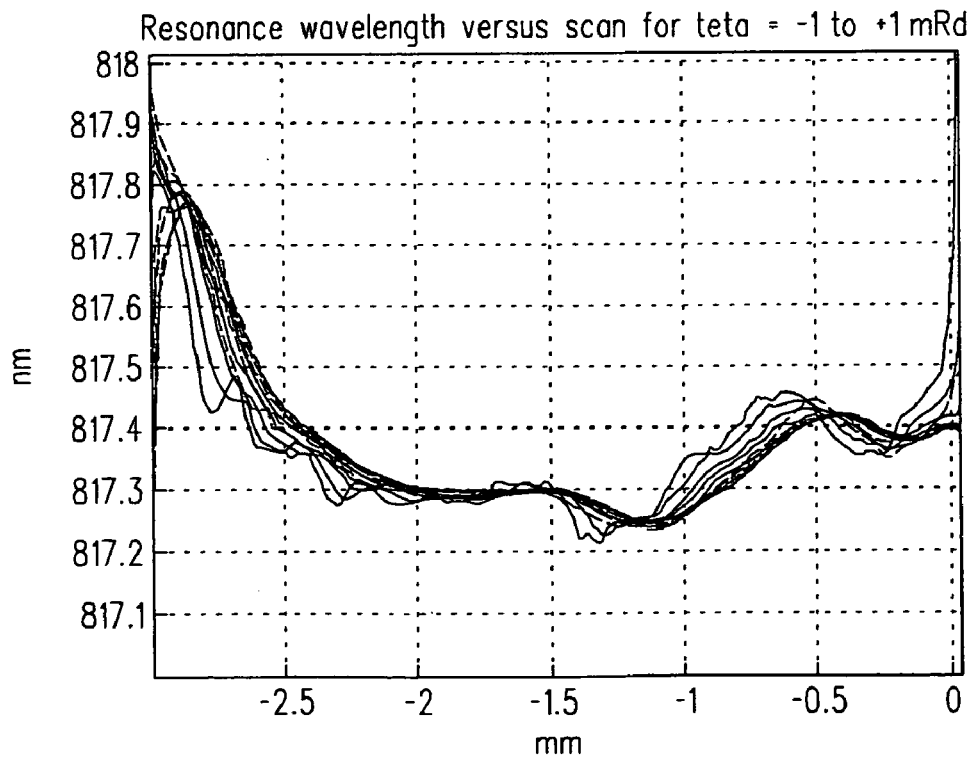
FIGS. 24-35 are graphs that are used to illustrate the results of an experiment which was conducted to further test the capabilities of the optical reader system to minimize angular and translational sensitivities when interrogating the resonant waveguide grating biosensor in accordance with the present invention.
Figure 25:
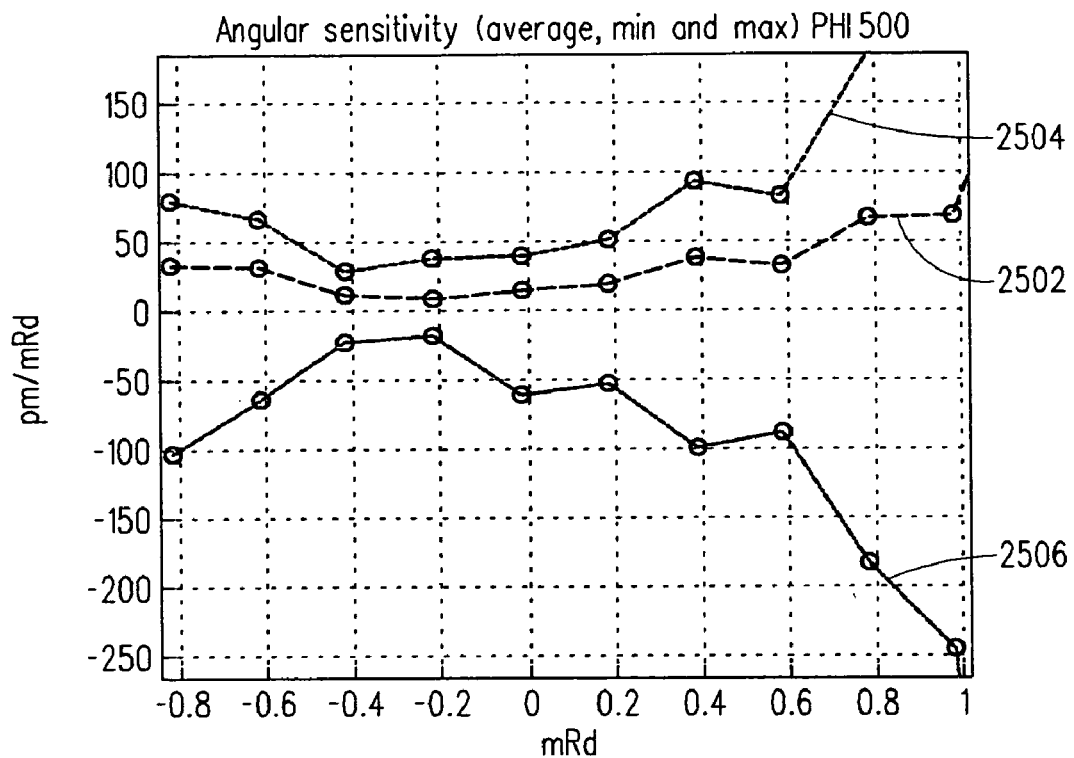

1. Angular Sensitivity in Static Conditions 1.1 Large Beam Diameter & Normal Incidence FIG. 24 is a graph that shows the typical shape of the resonance wavelength that was measured across a 3 mm biosensor 102 with a 500 microns diameter interrogating beam 104 at normal incidence. Each of the curves corresponds to a different angular misalignment. The "solid line" curves are for positive angles while the "dashed line" curves are for negative angles. It can be observed from this graph that the angular dependence of the wavelength was a function of the position across the biosensor 102. In this case, for instance, the dλ/dθ was very small around the middle of the biosensor 102 and was much bigger everywhere else. From this data, one can calculate the angular sensitivity expressed in pm/mRd as a function of the position across the biosensor 102 as shown in FIG. 25. In this graph, the curve 2502 indicates the average sensitivity across the biosensor 102. And, the curves 2504 and 2506 respectively indicate the MAX and MIN sensitivities across the biosensor 102.

To calculate the impact of an angular misalignment upon the measurement, one must determine dλ/dθ at the "measurement" location and at the "reference" location of a sensor. Sometimes, one may be lucky and dλ/dθ may be equal at both spatial locations but this is not guaranteed. The worst case corresponds to the case where dλ/dθ is maximum for one and minimum for the other. So, although the average dλ/dθ is close to 15 pm/mRd, the impact on the measurement accuracy might be up to 100 pm/mRd at 0 mRd incidence. Moreover, although the average curve appears to be quite repeatable from one biosensor 102 to another one, the MAX and MIN values can significantly change making the results even worse.

1.2 Small Beam Diameter & Normal Incidence

Figure 26:
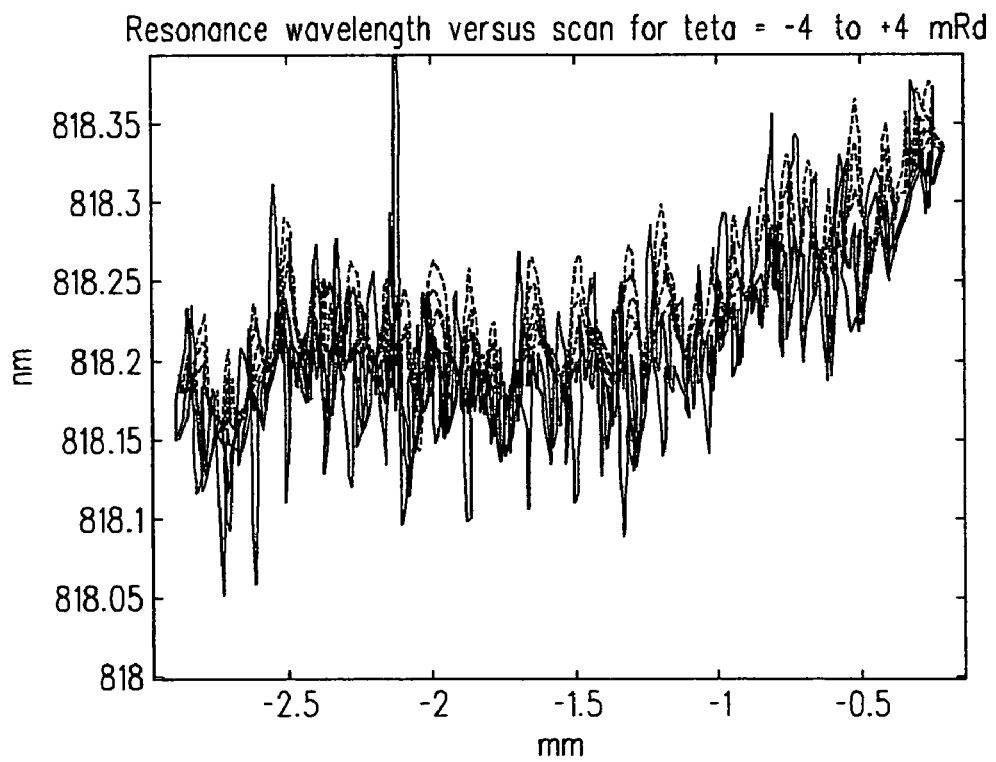
Figure 27:
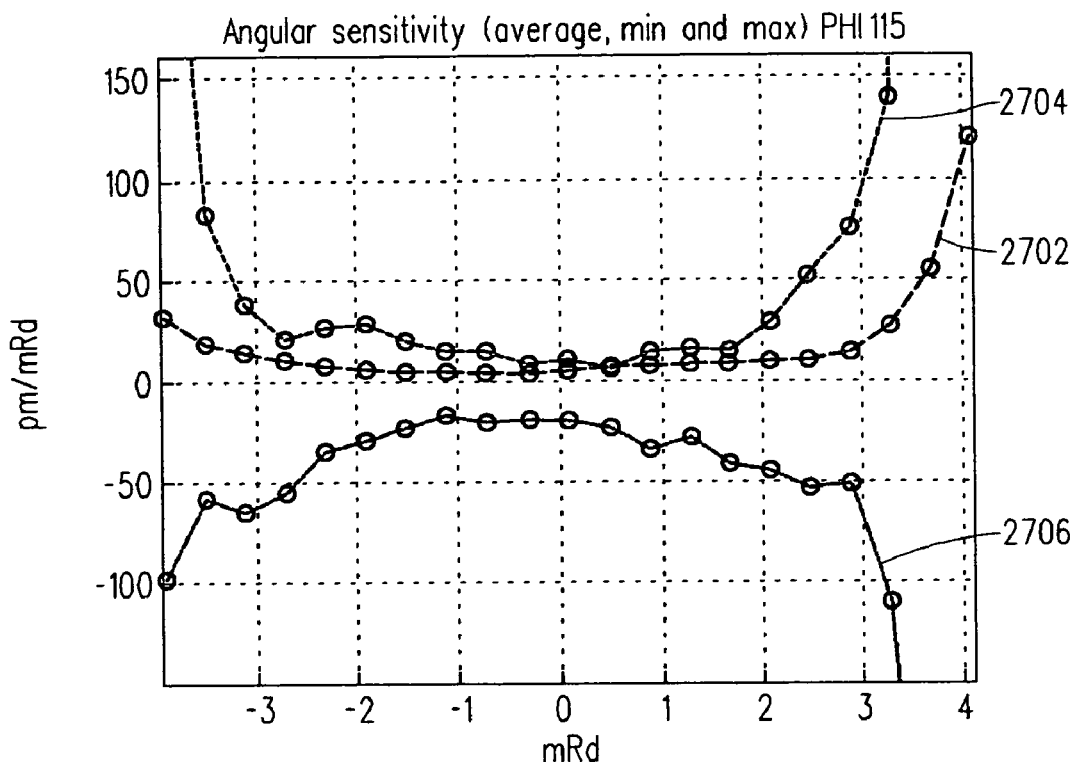

Next, a smaller beam 104 was used where "small" means much smaller than the distance over which the beam 104 is scanned. And, the following curves shown in FIG. 26 illustrate the resonance wavelength across the biosensor 102. The "solid line" curves are the positive angles and the "dashed line" curves are the negative angles. Again, it can be seen in this graph that dλ/dθ is also dependent on the location where the optical beam 104 hits the biosensor 102. The major difference is that those variations happened at much higher spatial frequencies when compared to FIG. 24. Then, as shown in FIG. 27, the average 2702, MAX 2704 and MIN 2706 of the angular dependence over the biosensor 102 can be calculated. As one can see, the angular sensitivity remained relatively constant over a range of +/−1 mRd. And, the average sensitivity around normal incidence was around 7 pm/mRd and, in the worst case, the measurement sensitivity in static conditions to angular misalignments was around 30 pm/mRd.

2.0 Angular Sensitivity in Dynamic Conditions 2.1 Small Beam Diameter & Normal Incidence An advantage of scanning the biosensor 102 is that, by averaging the data over large areas, all variations that have spatial periods less than the scanning range can be averaged. So, the problem of the difference between dλ/dθ at the reference position and at the measurement position drastically decrease.

Figure 28:
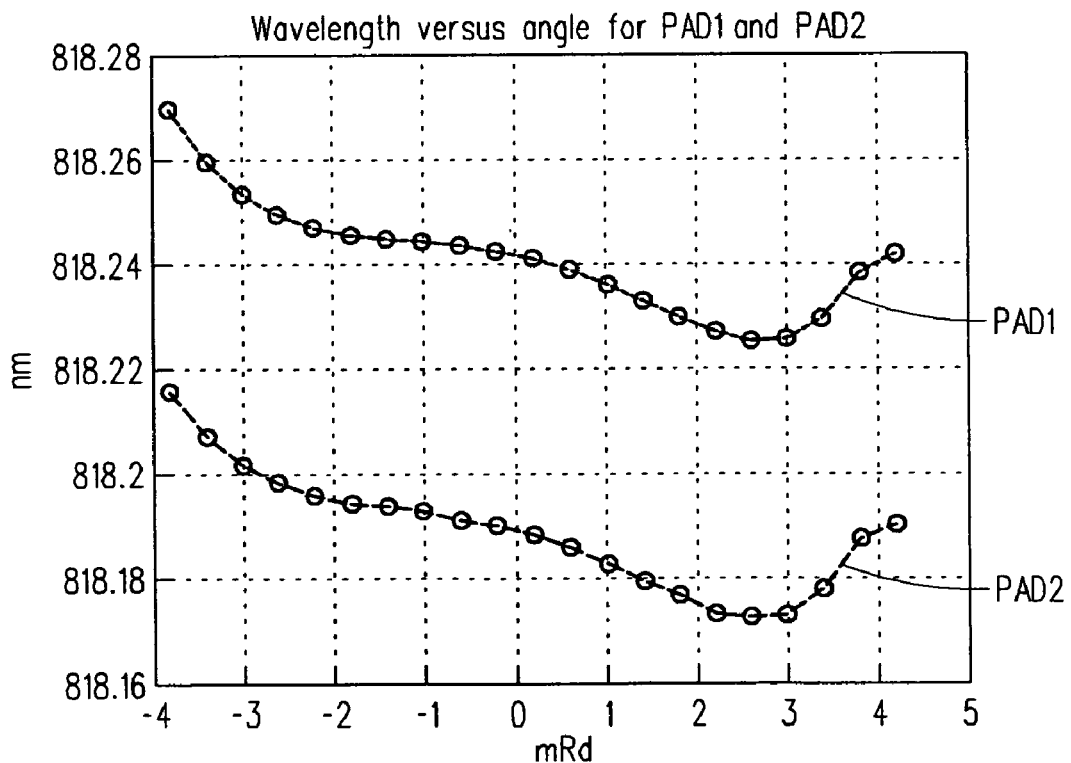
Figure 29:
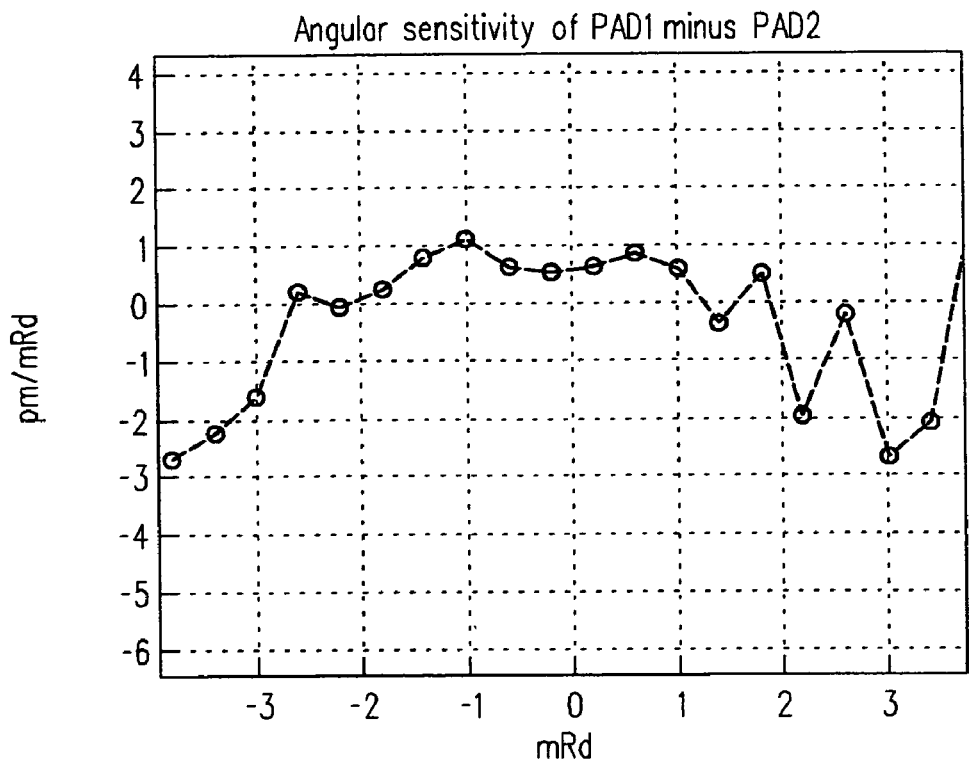

FIG. 28 is a graph that shows the evolution of resonances calculated as the spatial average over the first half (PAD1) and the second half (PAD2) of the biosensor 102. All measurements were obtained using 3 mm long biosensors 102. As can be seen, both signals have some angular dependence. However, both curves are very similar which means that there is likely to be some kind of systematic angular variations associated with the aberrations of the fibers to sensor imaging lens. FIG. 29 is a graph that shows a global measurement angular sensitivity curve which was obtained after subtracting the signals associated with PAD1 and PAD2. As can be seen, the angular sensitivity that is below 1 pm/mRd over an angular range of +/−2 mRd.

2.2 Large Beam Diameter & Normal Incidence

Figure 30:
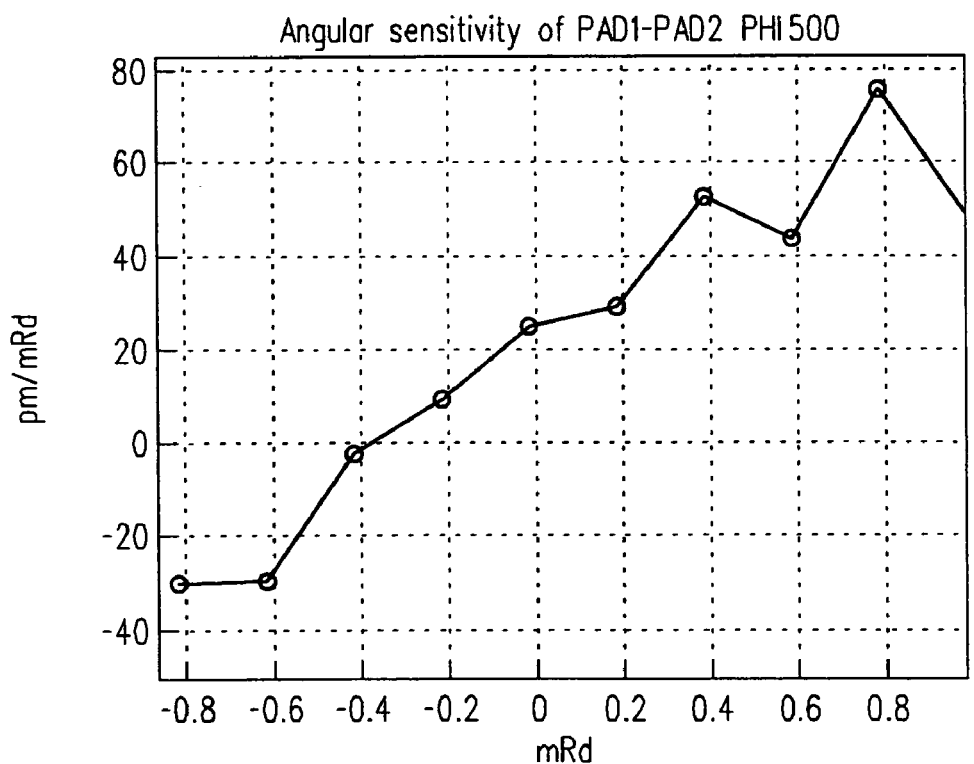

One can apply the same logic to the case of a 500 microns beam diameter. The problem with this case is that the period of the variations are of the same order of magnitude than the length of the scan so that the impact of averaging over half of the biosensor 102 does not work as well as in the previous case as can be seen in FIG. 30.

3.0 Lateral Sensitivity in Static Conditions

One can use the same curves as above to determine the sensitivity to lateral displacement. In this case, the angle was fixed and we calculated for each angle the amplitude of dλ/dx.

Figure 31:
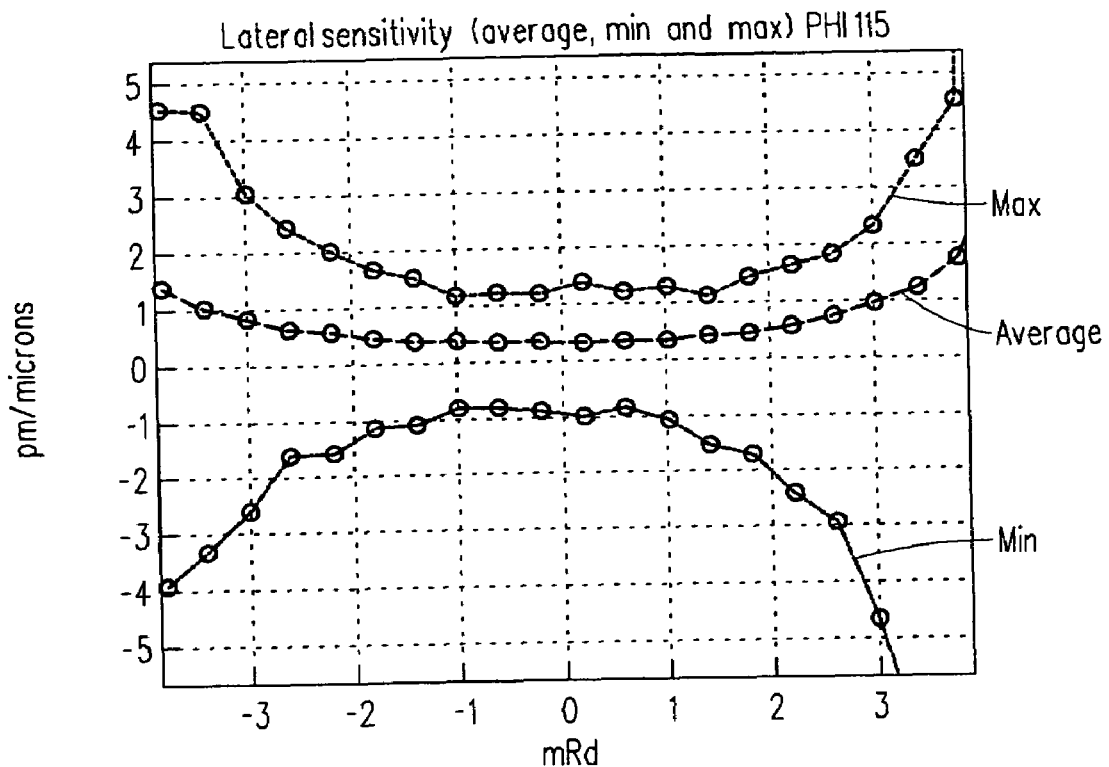

FIG. 31 shows the dλ/dx that was measured at normal incidence as a function of the angular misalignment of the microplate 516. As can be seen, there is an average dλ/dx of around 0.4 pm/microns close to normal incidence and, in the worst case, the impact on the measurement accuracy was up to 2.4 pm/microns. These sensitivities remained relatively constant over an angular range of +/−1 mRd but became worst for higher misalignments.

Figure 32:
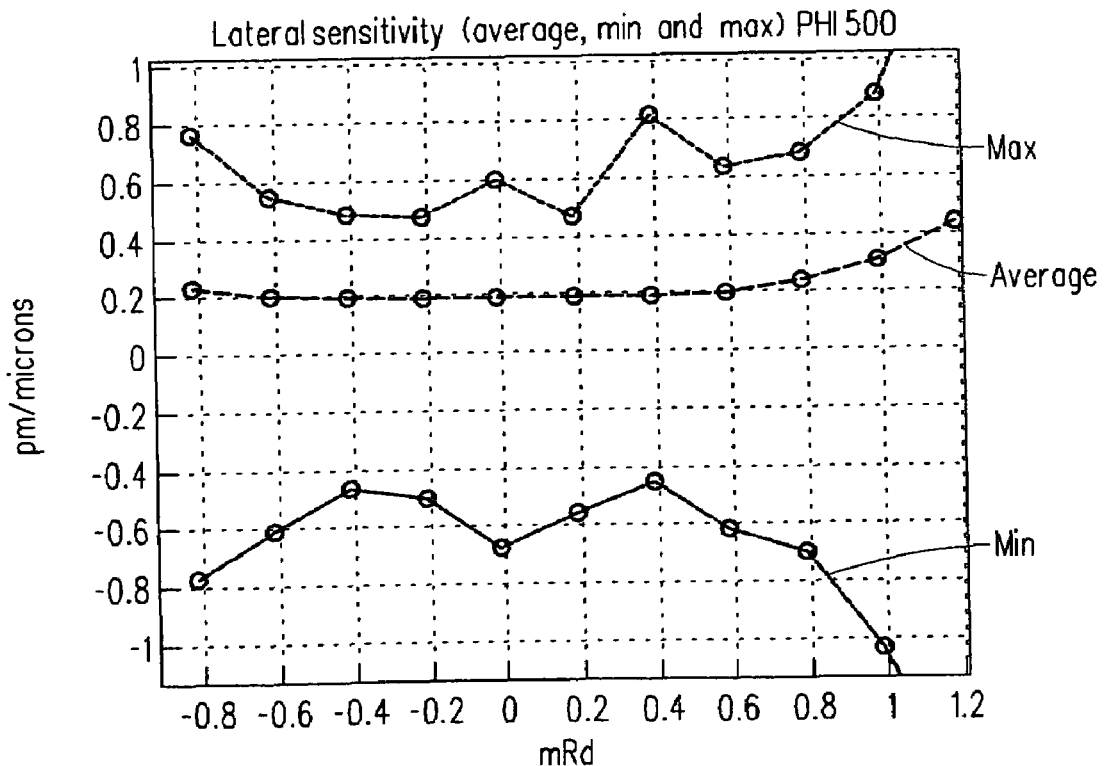

FIG. 32 represents the same data measured with a beam size of 500 microns. As can be seen, the sensitivities were lower by a factor of approximately 2 with an average of 0.2 pm/microns and a worst case of around 1 pm/micron.

4. Lateral Sensitivity in Dynamic Conditions

Figure 33:
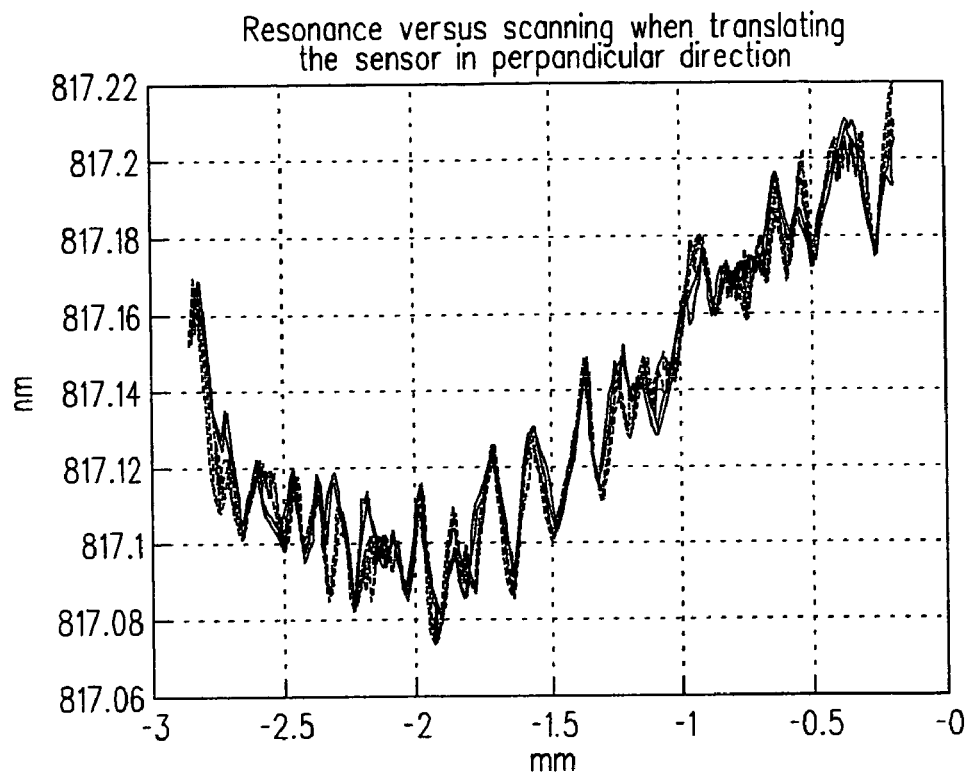
Figure 34:
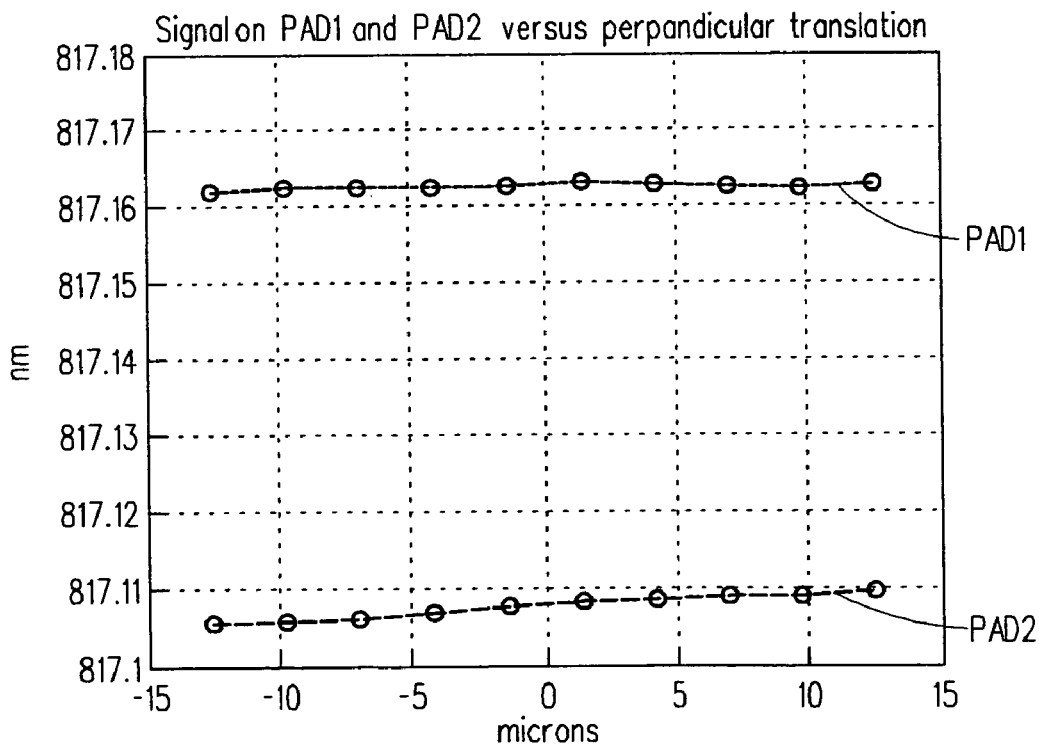
Figure 35:
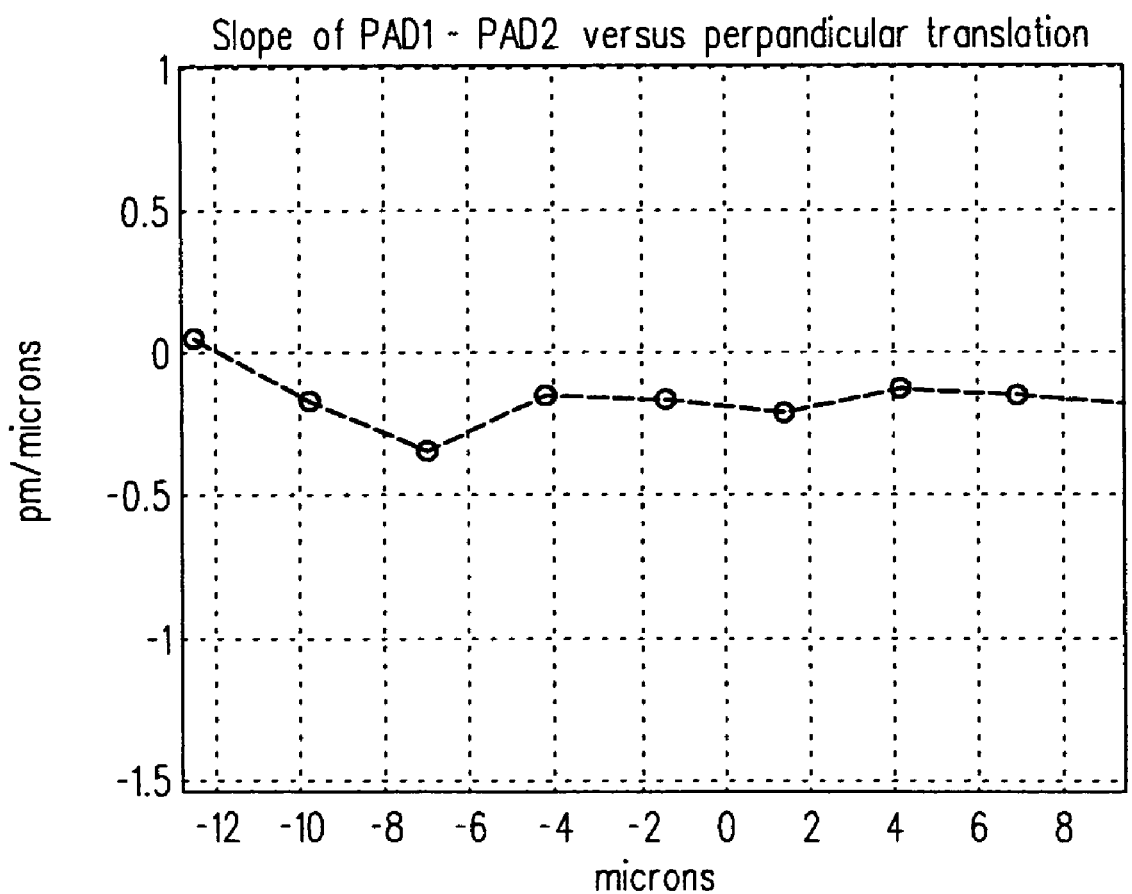

For angular sensitivity, the idea is that by integrating the signal over relatively large sub-areas (PADS 1 & 2) of the biosensor 102, one can then average the dλ/dθ. FIG. 33 is a graph which shows the resonance as a function of a scan position that was measured with a 115 microns spot size. During the measurement, the collimator (focusing optic) was intentionally misaligned by 2 mRd. The different curves correspond to the curves when translating the collimator by 2.5 microns in a direction perpendicular to the scanning. As can be seen, even though the curves have the same shape, the translation over a 25 microns full range, quantitatively impacts the measurement result. From these curves, we calculated the integral of the signal on PAD1 and PAD2 as a function of the lateral motion as shown in FIG. 34. And, then by calculating the difference between PAD1 and PAD2, we determined the measurement lateral sensitivity as shown in FIG. 35. In this case, the lateral sensitivities were in the range of 0.2 to 0.3 pm/micron which is much lower than one can get with static measurement methods.

5. Conclusion

In this experiment, the static configuration and the dynamic configuration were tested. And, for each of these configurations, two different beam sizes were investigated.

In reviewing, the measurement angular sensitivity data it can be concluded the scanning approach with a small beam in accordance with the present invention resulted in an impressive improvement as can be seen in TABLE #1.

TABLE #1

| | Angular sensitivities (pm/mRd) | |
|---|---|---|
| | PHI = 115 microns | PHI = 500 microns |
| Static (worst case) | 30 | 100 |
| Scanning | 1 | 22 |

If the sensitivity to lateral translation is analyzed, then one can conclude that small beam/scanning also achieves better performance as shown in TABLE #2.

TABLE #2

| | Lateral sensitivities (pm/microns) | |
|---|---|---|
| | PHI = 115 microns | PHI = 500 microns |
| Static (worst case) | 2.4 | 1 |
| Scanning | 0.3 | Not measured |

Additional 2-Dimensional Scan Experiment

Figure 36:
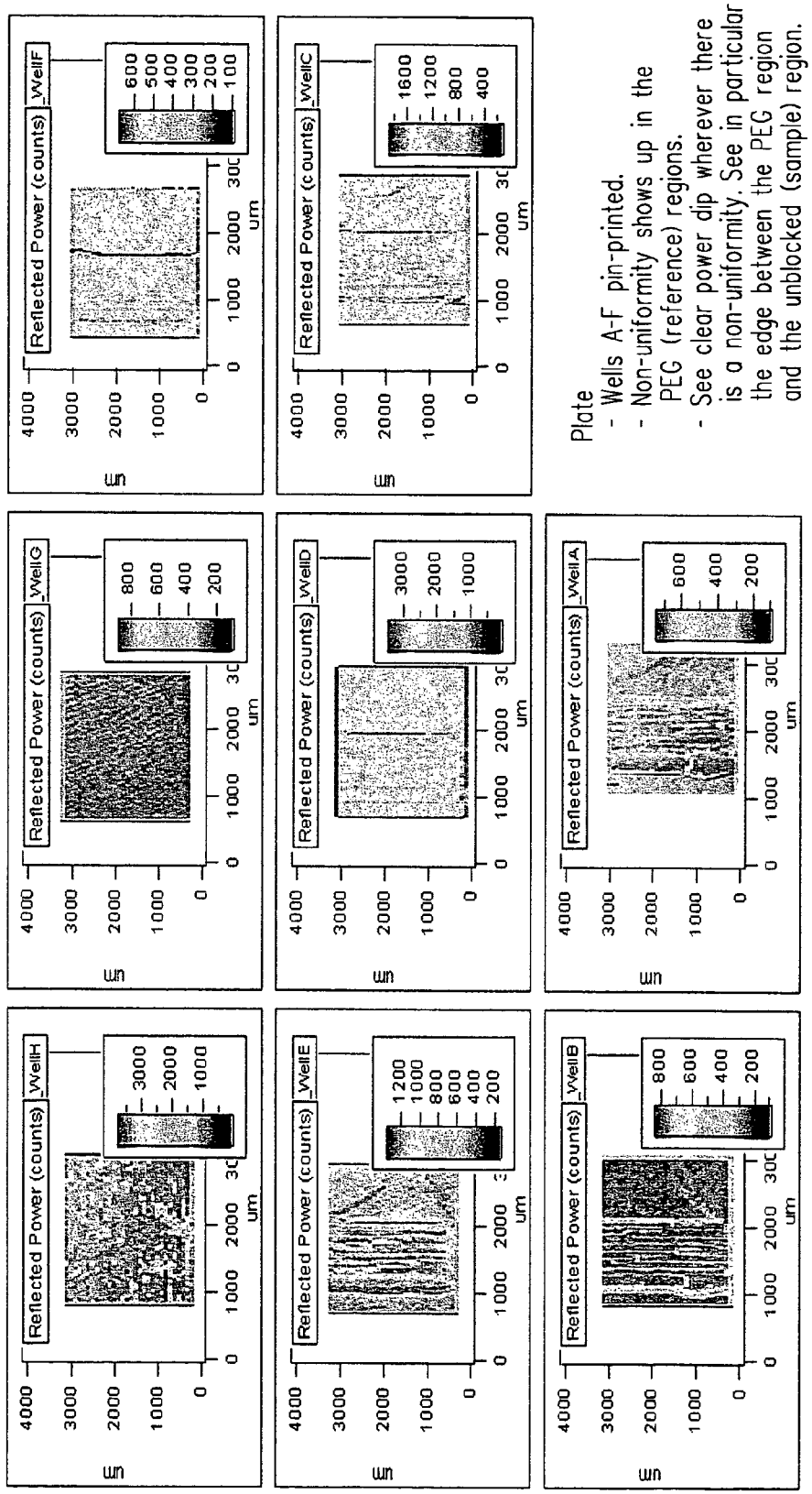
FIGS. 36-37 are graphs that are used to illustrate the results of an experiment which was conducted to test the 2-dimensional scan capabilities of the optical reader system in accordance with the present invention.
Figure 37:
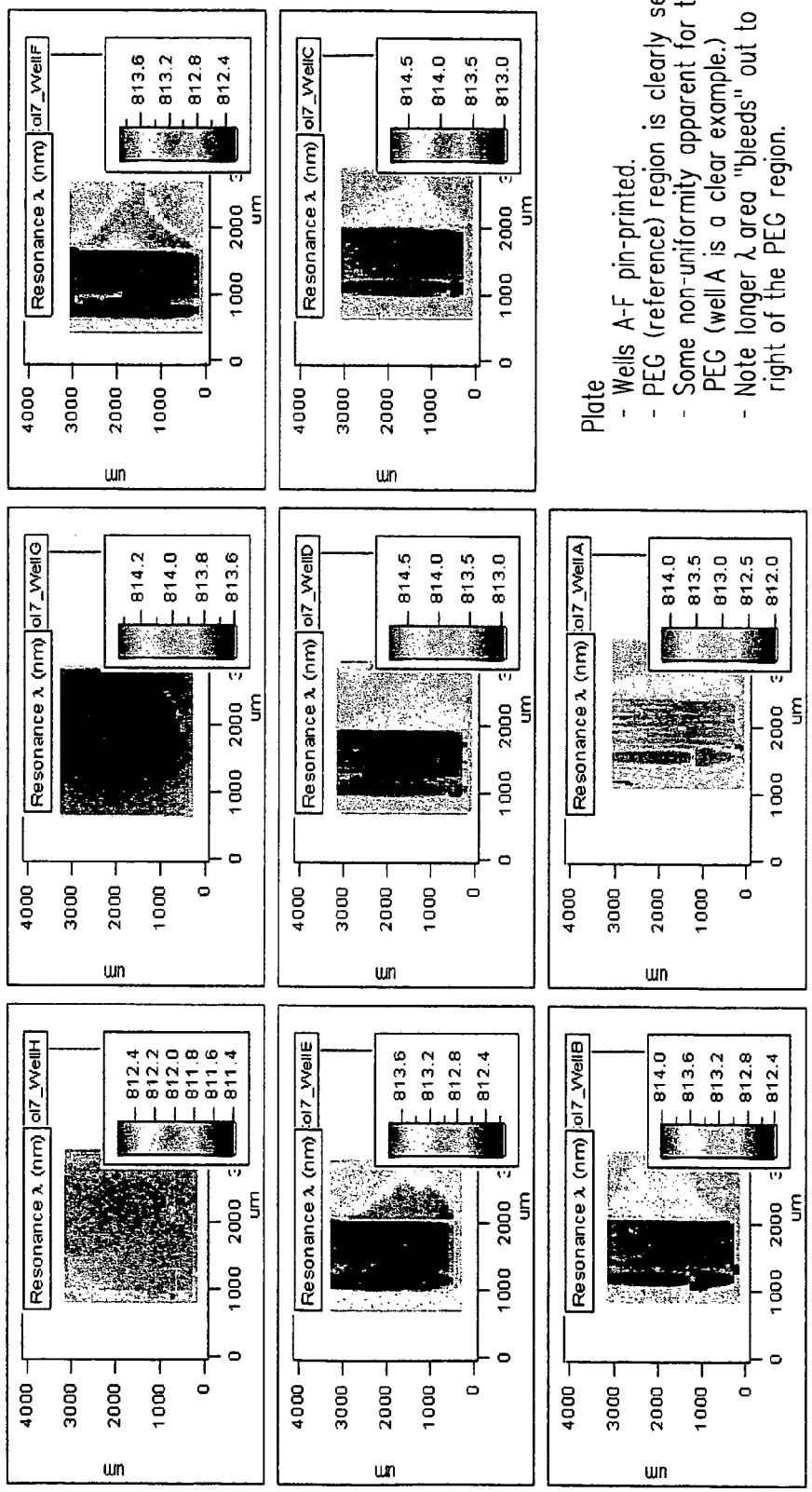

It was briefly mentioned above how the optical reader system 100 can be used to perform a 2-D scan of a biosensor 102. To prove the feasibility of this feature an experiment was performed in which the optical reader system 100' was in a 2-D scanning mode. In this mode, a linear scan was taken across a biosensor, the microplate 516 was then stepped over by approximately one optical beam width in a direction perpendicular to the linear scan, and the linear scan was repeated, and so on. FIGS. 36 and 37 contain 2D images from this experiment, obtained for reflected power and reflected wavelength, respectively. It should be noted how the 2D scan adds clarity to how a "picture" can be assembled, and to how binding and non-binding regions 702 and 704 may be identified on a biosensor 102'.

Some additional features and advantages of using the scanned optical reader system 100 and 100' to interrogate/characterize the biosensor 102 and 102' are described below as follows:

1) Scanning a small optical beam across a RWG biosensor allows one to spatially map the reflected power and wavelength (angle) of the sensor in order to better characterize the biosensor. This mapping allows one to find the location of the sensor very accurately, to create a map of sensor response as a function of position, to spatially average the response of the sensor, and to identify and exclude regions of the sensor which are deemed unacceptable.

2) The use of a scanned optical beam also allows one to easily interrogate signal and reference regions of a sensor. The use of signal and reference regions of a sensor, located in close proximity, can be used to remove undesired sensor related wavelength changes caused by thermal changes, bulk index of refraction changes, drift, and non-specific binding.

3) By scanning the same optical beam across the signal and reference regions of the biosensor, one can separate, via time, the optical signals from the signal and reference regions which may overlap significantly in wavelength. This allows one to utilize a single optical detector to detect both the binding and reference signals, which is not possible if the spectra of the binding and reference signals overlap and the binding and reference regions reflect identical polarization states.

4) A scanned optical beam allows one to eliminate a number of optical system related issues that may lead to false wavelength changes. By using the same optical path for interrogating both the signal and reference portions of a biosensor, the system can greatly reduce or cancel out changes in wavelength that arise from angular changes between the biosensor and optics. By using the edges of the sensor or built in fiducial markings on the sensor plate, the scanned optical system can measure the absolute translational position of a biosensor to high accuracy, and hence correct for movements of the plate which can alter wavelength. Additionally, one can greatly reduce or eliminate changes in perceived wavelength that arise from changes in the optical path or drifts of the detector, since the signal and reference share a common path and detector.

5) A scanned optical beam may be used to interrogate a patterned array of multiple biochemical targets placed on the same grating, enabling multiplexing of assays using a single RWG biosensor. The use of optical beam scanning allows the different target signals to be separated in time and correlated with a specific position on the biosensor.

6) The architecture of the optical reading system can be used even if the wavelengths and polarizations of the binding and reference regions are not precisely controlled, or even if the wavelengths are identical. This scanning technique also has additional benefits of being able to remove false wavelength changes that may arise from the biosensor being physically displaced or altered in its angular orientation, and other undesired wavelength changes that may derive from drift of the optical detector itself.

7) In the present invention the spectra collection can be precisely timed based on the position of the scanner. This enables one to collect spectra while moving without requiring an ultra stable scan velocity. Also, one can utilize the amount of time between spectra collections in the algorithm to reject the "velocity jitter" of the scanning stage.

It should be noted that in most of the drawings herein, were made based on the assumption that the sensor is spectrally interrogated. This means that the sensor is interrogated at a fixed incidence angle with a broad spectral source and that the wavelength is detected in the reflected beam. The source is then a broad spectral source and the detector is a wavelength sensitive detector such as a spectrometer. However, it should be appreciated that the principle of the present invention can also be extended to an angular interrogation approach where the sensor is interrogated with monochromatic light and then a resonant angle is detected in the reflected beam.

Although multiple embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:

1. A system comprising:
a biosensor; and
a label-free optical reader system which includes:
   a light source that outputs a first optical beam which is smaller than the biosensor and is scanned across the biosensor;
   a detector that collects a second optical beam reflected from the biosensor while the first optical beam is being scanned across the biosensor; and
   a processor that processes the collected second optical beam to obtain raw spectral/angular data that is a function of a position on the biosensor; and
said biosensor has a waveguide formed from a substrate, a diffraction grating and a waveguide film, wherein the biosensor has at least one reference region on which target molecules cannot bind and at least one sample region on which the target molecules can bind, wherein the at least one reference region and the at least one sample region are formed in a predefined pattern, wherein the raw spectral/angular data associated with the at least one sample region is used to perform a label-free detection of a biomolecular binding event and the raw spectral/angular data associated with the at least one reference region is used to reference out spurious changes that can adversely affect the label-free detection of the biomolecular binding event, wherein said biosensor has at least one diagonal cut located at a diagonal angle across features which make-up the diffraction grating wherein the diagonal cut enables the use of a 1-dimensional beam scan to estimate both an x and y location of said biosensor relative to said label-free optical reader system.

2. The system of claim 1, wherein the predefined pattern is a striped pattern or a checkerboard pattern.

* * * * *